(12) United States Patent
Castelli

(10) Patent No.: US 12,070,453 B2
(45) Date of Patent: Aug. 27, 2024

(54) TREATMENT OF FABRY DISEASE IN ERT-NAÏVE AND ERT-EXPERIENCED PATIENTS

(71) Applicant: Amicus Therapeutics, Inc., Philadelphia, PA (US)

(72) Inventor: Jeff Castelli, New Hope, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

(21) Appl. No.: 16/318,905

(22) PCT Filed: Jul. 19, 2017

(86) PCT No.: PCT/US2017/042872
§ 371 (c)(1),
(2) Date: Jan. 18, 2019

(87) PCT Pub. No.: WO2018/017721
PCT Pub. Date: Jan. 25, 2018

(65) Prior Publication Data
US 2019/0183869 A1 Jun. 20, 2019

Related U.S. Application Data

(63) Continuation-in-part of application No. 15/213,920, filed on Jul. 19, 2016, now Pat. No. 9,999,618.

(51) Int. Cl.
*A61K 31/445* (2006.01)
*A61K 31/45* (2006.01)
*A61K 31/7008* (2006.01)

(52) U.S. Cl.
CPC ............ *A61K 31/445* (2013.01); *A61K 31/45* (2013.01); *A61K 31/7008* (2013.01)

(58) Field of Classification Search
None
See application file for complete search history.

(56) References Cited

U.S. PATENT DOCUMENTS

| | | | |
|---|---|---|---|
| 5,900,360 A | 5/1999 | Welch et al. | |
| 6,270,954 B1 | 8/2001 | Welch et al. | |
| 6,274,597 B1 | 8/2001 | Fan et al. | |
| 6,541,195 B2 | 4/2003 | Welch et al. | |
| 6,583,158 B1 | 6/2003 | Fan et al. | |
| 6,589,964 B2 | 7/2003 | Fan et al. | |
| 6,599,919 B2 * | 7/2003 | Fan ................ | A61K 31/70 514/315 |
| 6,774,135 B2 | 8/2004 | Fan et al. | |
| 6,916,829 B2 | 7/2005 | Fan et al. | |
| 7,141,582 B2 | 11/2006 | Fan et al. | |
| 2004/0180419 A1 | 9/2004 | Fan | |
| 2005/0137223 A1 | 6/2005 | Fan et al. | |
| 2006/0287358 A1 | 12/2006 | Wustman | |
| 2010/0004156 A1 | 1/2010 | Kaushal et al. | |

FOREIGN PATENT DOCUMENTS

| | | |
|---|---|---|
| AU | 2015230773 A1 | 12/2015 |
| CA | 2086413 A1 | 12/1991 |
| JP | 2013255488 A | 12/2013 |
| WO | 90/11353 A1 | 10/1990 |
| WO | 2004/074450 A2 | 9/2004 |
| WO | 2006/125141 A2 | 11/2006 |
| WO | 2007013072 A1 | 2/2007 |
| WO | 2008/034628 A1 | 3/2008 |
| WO | 2008121826 A2 | 10/2008 |

OTHER PUBLICATIONS

Giraldo et al. Haematologica (2009), vol. 94, pp. 1771-1775.*
Pastores et al. Expert Opinion on Emerging Drugs (2005), vol. 10, p. 891-902.*
Ino et al. Journal of Drug Assessment (2013), vol. 2, pp. 87-93.*
Schiffmann, Raphael, et al. "Improvement in gastrointestinal symptoms observed in the phase 3 Facets (AT1001-011) study of migalastat in patients affected with Fabry disease." Molecular Genetics and Metabolism 2.114 (2015): S103-S104.*
Ishii, Satoshi. "Pharmacological chaperone therapy for Fabry disease." Proceedings of the Japan Academy, Series B 88.1 (2012): 18-30.*
Ishii, Satoshi, et al. "Mutant α-galactosidase A enzymes identified in Fabry disease patients with residual enzyme activity: Biochemical characterization and restoration of normal intracellular processing by 1-deoxygalactonojirimycin." Biochemical Journal 406.2 (2007): 285-295.*
EU Clinical Trials Register, Feb. 13, 2006, https://www.clinicaltrialsregister.eu/ctr-search/trial/2006-000181-36/GB, 1-4.
EU Clinical Trials Register, Oct. 17, 2005, https://www.clinicaltrialsregister.eu/ctr-search/trial/2005-004384-33/GB, 1-4.
NCT00214500 on Sep. 21, 2005: https://clinicaltrials.gov/archive/NCT00214500/2005_09_21, Sep. 21, 2005, https://clinicaltrials.gov/archive/NCT00214500/2005_09_21, 1-3.
NCT00283933 on Jan. 30, 2006: ClinicalTrials.gov Archive, Jan. 30, 2006, https://clinicaltrials.gov/archive/NCT00283933/2006_01_30, 1-3.
NCT00283959 on Jan. 30, 2006: ClinicalTrials.gov Archive, Jan. 30, 2006, https://clinicaltrials.gov/archive/NCT00283959/2006_01_30, 1-3.
NCT00304512 on Mar. 17, 2006: ClinicalTrials.gov Archive, Mar. 17, 2006, https://clinicaltrials.gov/archive/NCT00304512/2006_03_17, 1-4.
Final Office Action in U.S. Appl. No. 11/749,512, dated Jun. 16, 2010, 13 pages.
Final Office Action in U.S. Appl. No. 12/966,904, dated Jan. 12, 2012, 10 pages.

(Continued)

Primary Examiner — Patrick T Lewis
(74) Attorney, Agent, or Firm — Servilla Whitney LLC

(57) ABSTRACT

Provided are dosing regimens for the treatment of Fabry disease in a patient. Certain methods relate to the treatment of ERT-experienced or ERT-naïve Fabry patients. Certain methods comprise administering to the patient about 123 mg free base equivalent of migalastat for improving left ventricular mass and/or improving podocyte globotriaosylceramide.

17 Claims, 14 Drawing Sheets

Specification includes a Sequence Listing.

(56) References Cited

OTHER PUBLICATIONS

Final Office Action in U.S. Appl. No. 13/445,338, dated Sep. 11, 2013, 9 pages.
"Galafold Summary of Product Characteristics", May 2016, 45 pgs.
Invitation to Pay Additional Fees and, Where Applicable, Protest Fee in PCT/US2017/042872 dated Oct. 11, 2017, 15 pages.
Journal of Inherited Metabolic Disease, 2015, vol. 38, No. 1, Suppl, p. S56.
Molecular Genetics and Metabolism, 2015, vol. 114, No. 2, pp. S57.
Non-Final Office Action in U.S. Appl. No. 11/749,512, dated Nov. 18, 2009, 10 pages.
Non-Final Office Action in U.S. Appl. No. 12/966,904, dated May 17, 2011, 11 pages.
Non-Final Office Action in U.S. Appl. No. 13/445,338, dated Feb. 5, 2013, 7 pages.
Non-Final Office Action in U.S. Appl. No. 16/011,063, dated Apr. 26, 2019, 21 pages.
Non-Final Office Action in U.S. Appl. No. 16/011,075, dated Apr. 26, 2019, 21 pages.
Non-Final Office Action in U.S. Appl. No. 14/713,821 dated Mar. 15, 2016, 10 pages.
PCT International Search Report and Written Opinion in PCT/US2017/042872 dated Jan. 3, 2018, 19 pages.
PCT International Search Report for PCT/US08/61764 dated Oct. 7, 2008, 2 pages.
PCT Invitation to Pay Additional Fees And, Where Applicable, Protest Fee in PCT/US2017/042864 dated Feb. 28, 2018, 16 pgs.
Pharmacological chaperone corrects lysosomal storage in Fabry disease caused by trafficking-incompetent variants, American Journal of Physiology-Cell Physiology, vol. 290, No. 4, pp. C1076-C1082 (2006).
Supplemental European Search Report in EP 07797506.8, dated Feb. 15, 2010.
Supplemental European Search Report in EP 08747020.9, dated Aug. 10, 2010.
Andersson, Hans C., et al., "Individualization of Long-Term Enzyme Replacement Therapy for Gaucher Disease", Genetics in Medicine, 2005, vol. 7, No. 2, pp. 105-110.
Bishop, et al., "Human Alpha-Galactosidase A: Nucleotide Seqence of a cDNA Clone Encoding the Mature Enzyme", Proc. Natl. Acad. Sci. USA vol. 83, 1986, 4859-4863.
Bishop, et al., "Molecular Genetics", Am. J. Hum. Genet. vol. 37, 1985, p. A144.
Brady, et al., "Enzymatic Defect in Fabry's Disease. Ceramidetrihexosidase Deficiency", N. Engl. J. Med. vol. 276, 1967, 1163-1167.
Branum, et al., "Effect of Two Anticoagulants on Leukocyte Yield and Function, and on Lysosomal Enzyme Activity", Clin. Chem. vol. 34 No. 1, 1988, 110-113.
Brooks, Doug A., "Getting Into the Fold", Nature Chemical Biology 2007, vol. 3, No. 2, pp. 84-85.
Brown, et al., "Strategies for Correction the Delta F508 CFTR Protein-Folding Defect", Journal of Bioenergetics and Biomembranes vol. 29 No. 5, 1997, 491-502.
Butters, T. D., "Expert Opin. Pharmacother., 2007, vol. 8, No. 4,, pp. 427-435".
Calhoun, et al., "Fabry Disease: Isolation of a cDNA Clone Encoding Human Apha-Calactosidase A", Proc. Natl. Acad. Sci. USA vol. 82, 1985, 7364-7368.
Davies, et al., "Fabry Disease: Fourteen Alpha-Galactosidase A Mutations in Unrelated Families From the United Kingdom and Other European Countries", Eur. J. Hum. Genet. vol. 4, 1996, 219-224.
Desnick, et al., "Metabolic and Molecular Bases of Inherited Disease", Scriver, et al. (eds.) 8th ed., Graw-Hill, New York, 2001, 3733-3774.
Eng, et al., "Fabry Disease: Thirty-Five Mutations in the Alpha-Galactosidase A Gene in Patients with Classic and Variant Phenotypes", Mol. Med. vol. 3, 1997, 174-182.

Eng, et al., "Nature and Frequency of Mutations in the Alpha-Galactosidase A Gene That Cause Fabry Disease", Am. J. Hum. Genet. vol. 53, 1993, 1186-1197.
Fan, Jian-Qiang, et al., "A contradictory treatment for lysosomal storage disorders: inhibitors enhance mutant enzyme activity", Trends in Pharm. Sci. vol. 24 No. 7, Jul. 2003, 355-360.
Fan, Jian-Qiang, et al., "Accelerated transport and maturation of lysosomal alpha-galactosidase A in Fabry lymphoblasts by an enzyme inhibitor", Nat. Med. vol. 5 No. 1, 1999, 112-115.
Frustaci, Andrea, et al., "Improvement in Cardiac Function in the Cardiac Variant of Fabry's Disease with Galactose-Infusion Therapy", New England Journal of Medicine, 2001, vol. 345, No. 1, pp. 25-32.
Fuller, et al., "Urinary Lipid Profiling for the Identification of Fabry Hemizygotes and Heterozygotes", Clinical Chemistry vol. 51, 2005, 688-694.
Germain, D. P., et al., "Treatment of Fabry's Disease with the Pharmacological Chaperone Migalastat", The New England Journal of Medicine, Aug. 11, 2016, 11.
Giraldo, Pilar, et al., Real-world clinical experience with long-term miglustat maintenance therapy in type 1 Gaucher disease: the Zagal project, 2009, 1771-1775.
Giugliani, R., et al., A Phase 2 study of migalastat hydrochloride in fenlales with Fabry disease: Selection of population, safety and pharmacodynanlic effects, Molecular Genetics and Metabolism, Academic Press, Amsterdam, NL, vol. 109, No. 1, Jan. 26, 2013, pp. 86-92.
Guerard, Nicolas, et al., "Lucerastat, an Iminosugar for Substrate Reduction Therapy: Pharmacokinetics, Tolerability, and Safety in Subjects With Mild, Moderate, and Severe Renal Function Impairment", The Journal of Clinical Pharmacology, 2017, 1425-1431.
Guerard, Nicolas, et al., "Lucerastat, an Iminosugar for Substrate Reduction Therapy: Tolerability, Pharmacodynamics, and Pharmacokinetics in Patients With Fabry Disease on Enzyme Replacement", Clinical Pharmacology & Therapeutics, Apr. 2018, 703-711.
Guerard, N., et al., "Lucerastat, an Iminosugar with potential as substrate reduction therapy for glycolipid storage disorders: safety, tolerability, and pharmacokinetics in healthy subjects", Orphanet Journal of Rare Diseases, Jan. 14, 2017, 1-10.
Ishii, et al., "Aggregation of the Inactive Form of Human alpha-Galactosidase in the Endoplasmic Reticulum", Biochem. Biophys. Res. Comm. vol. 220, 1996, 813-815.
Ishii, Satoshi, et al., "Transgenic mouse expressing human mutant a-galactosidase A in an endogenous enzyme deficient background: a biochemical animal model for studying active-site specific chaperone therapy for Fabry disease", Biochimica et Biophysica Acta, vol. 1690, No. 3, (2004) pp. 250-257.
Kornreich, et al., "Nucleotide Sequence of the Human Alpha-Galactosidase A Gene", Nucleic Acids Res. vol. 17, 1989, 3301-3302.
Kusiak, et al., "Purification and Properties of the Two Major Isozymes of Apha-Galactosidase from Human Placenta", J. Biol. Chem. Vo. 253, 1978, 184-190.
Mayes, et al., "Differential Assay for Lysosomal Alpha-Galactosidases in Human Tissues and its Application to Fabry's Diesease", Clin. Chim. Acta vol. 112 No. 2, 1981, 247-251.
Mizukoshi, Kei, et al., Normal Values of Left Ventricular Mass Index Assessed by Transthoracic Three-Dimensional Echocardiography, Journal of the American Society of Echocardiography, vol. 29, No. 1, Jan. 2016, pp. 51-61.
Nakao, et al., "An Atypical Variant of Fabry's Disease in Men with Left Ventricular Hypertrophy", N. Engl. J. Med. vol. 333, 1995, 288-293.
Park, et al., "Long-Term Correction of Globotriaosylceramide Storage in Fabry Mice by Recombinant Adeno-Associated Virus-Mediated Gene Transfer", Proc. Natl. Acad. Sci. USA vol. 100, 2003, 3450-3454.
Sawkar, Anu R., et al., "Gaucher Disease-Associated Glucocerebrosidases Show Mutation-Dependent Chemical Chaperoning Profiles", Chemistry & Biology, vol. 12, Nov. 2005, 1235-1244.

(56) References Cited

OTHER PUBLICATIONS

Sawkar, A. R., et al., "Therapeutic Strategies to Ameliorate Lysosomal Storage Disorders—A Focus on Gaucher Disease", Cell. Mol. Life Sci. 63 (2006), pp. 1179-1192.

Shin, Sang H, et al., "Prediction of Response of Mutated alpha-Galactosidase A to a Pharmacological Chaperone", Pharmacogenet Genomics, vol. 18, No. 9, Sep. 2008, 773-780.

Shin, S, et al., "Screening for Pharmacological Chaperones in Fabry Disease", Materials and Methods vol. 359, 2007, 168-173.

Steet, Richard A., et al., "The iminosugar isofagomine increases the activity of N370S mutant acid beta-glucosidase in Gaucher fibroblasts by several mechanisms", PNAS, 2006, vol. 103, No. 37, pp. 13813-13818.

Tsuji , et al., "Signal Sequence and DNA-Mediated Expression of Human Lysosomal Alpha-Galactosidase A", Eur. J. Biochem. vol. 165, 1987, 275-280.

Weinberg , "Effect of Shipment, Storage, Anticoagulant, and Cell Separation on Lymphocyte Proliferation Assays for Human Immunodeficiency Virus-Infected Patients", Clin. Diagn. Lab. Immunol. Vol. 5 No. 6, 1998, 804-807.

Weinreb, Neal J., et al., "Guidance on the Use of Miglustat for Treating Patients with Type 1 Gaucher Disease", American Journal of Hematology 80, 2005, pp. 223-229.

Welch , et al., "Influence of Molecular and Chemical Chaperones on Protein Folding", Cell Stress and Chaperones vol. 1 No. 2, 1996, 109-115.

Yam, Gary Hin-Fai , et al., "A synthetic chaperone corrects the trafficking defect and disease phenotype in a protein misfolding disorder", The FASB Journal, 2004, 12-18.

Yam, Gary Hin-Fai , et al., "Pharmacological chaperone corrects lysosomal stroage in Fabry disease caused by trafficking-incompetent variants", Am. J. Physiol. Cell Physiol. Vol. 290, Apr. 2006, C1076-C1082.

Amicus Therapeutics, Inc., Annual Report Pursuant To Section 13 or 15(d) of the Securities Exchange Act Of 1934 (Form 10-K) (Mar. 3, 2015).

"Galafold EP Label Summary of Product Characteristics", May 2022, 59 pages.

"Galafold—migalastat hydrochloride capsule", Amicus Therapeutics US, LLC Dec. 15, 2022.

"Galafold U.S. Label, Revised Aug. 10, 2018, 24 pages".

* cited by examiner

```
cccttctgtaggggcagagaggttctacttcattactgcgtctcctgggaaggccatcag      60
gactgctggctaaagtgggaaccaggactctttgtgagttaagaatttgtgtatttatat     120
gtgtgttatacacattttttaaaaaactgtaacgacatcaggttgagcagtcgtctccgg     180
gtggtgaattatgtgtattttttaattttatactatattgttattttcaaatgttcgaa     240
attgaatatgtagattgttgttatcagcagaaaaataaacattattcaaatactctattc     300
agtaaagtaatttattgggcgcctttgtcaagcacgcatttgcctagatgtgactctaca     360
gataaaattcacttggggcctcccttacagacaatcaggcagtggagactgagtgcctg     420
aatggatagaccagcactcagaccactattttcagtatctgttttcttaactcagggcc     480
gtggttttcaaacgttttcgccttacggtcacccttagggtccccgagaccggcccag      540
acagacagatatacaaaaacacatacacagtcatgagcgtccaccatttccccaccaggc     600
gcagcacaggcggcttccggcactgagatggggggggaggagggagagagcgcgaggggg     660
gaggggaaagcagagaacgaaagaggcggaggcggccccgaaccccgctctggtcttca     720
tcatcaccaccctgggtccccagttcccacccacacaccaacctctaacgataccgggt     780
aattttcctccttcttccctcaaacggctatagcgagacggtagacgacgaccagaacta     840
cttctgctcacgtaagcgagtaatcacgtgagcgcctacgtcatgtgagatctcggtcac     900
gtgagcaactctcggcttaaactcgggatcactaaggtgccgcacttccttctggtatgg     960
aaatagggcgggtcaatatcaagaaaggaagagggtgattggttagcggaacgtcttacg    1020
tgactgattattggtctacctctggggataaccgtcccagttgccagagaaacaataacg    1080
tcattatttaataagtcatcggtgattggtccgcccctgaggttaatcttaaaagcccag    1140
gttacccgcggaaatttatgctgtccggtcaccgtgacaatgcagctgaggaacccagaa    1200
ctacatctgggctgcgcgcttgcgcttcgcttcctggccctcgtttcctgggacatccct    1260
ggggctagagcactggacaatggattggcaaggacgcctaccatgggctggctgcactgg    1320
gagcgcttcatgtgcaaccttgactgccaggaagagccagattcctgcatcaggtatcag    1380
atattgggtactcccttccctttgcttttccatgtgtttgggtgtgtttggggaactgga    1440
gagtctcaacgggaacagttgagcccgagggagagctccccacccgactctgctgctgc    1500
ttttttatccccagcaaactgtcccgaatcaggactagccctaaactttctctgtgtgac    1560
cttcctgggatgggagtccggccagcggcccctgtttctttctctctctctctctct      1620
cgttctccttctctttctctttctcttctttcctctctcttttctctctctccctgcccgg    1680
ttctcttttttcactgctccttgcagagcagggccaccccataggcagtgtgcccaaagt    1740
agccctgcccggttctattcagacccttcttgtgaacttctgctcttcctctgccgggtg    1800
ctaaccgttagaacatctagggtgggtaggaggaatggggaactaagattcgtgccattt    1860
tttctccttttggggtcgtggatttctcggcagtatctcgagggagttagagagaccata    1920
aggtcgctgagatctctcccacctcgcccatgagcgtggcatcaggctggaaggttgaca    1980
tggaggaactttatacatttacaccttgcgtgagggttgaggctggattagataggtat    2040
tgaacatatctgaccctcacaatccttatctgtaaattgggattacaaccttttaatttc    2100
agggagctgacaaaaaaatctgaaaatagttcttatctcacacaggtgagttttcaag     2160
gagataacctatttaaagtacatagcacagcgcttgaccattcaactgcgcttacagagc    2220
aaatgttcaatgggaaatgaatgtaaatctacaaatctgaatgaatatgtgtattttc     2280
tggagagaggatatttacctttcttcaaattctcaagggctctgtgatttaaaaaaggt    2340
taggaatcactgatagatgttggtaaaaggtggcagtcacagtacatttctgtgtccata    2400
agttattcctatgaatatctttatagataaagtcaggatgttggtcagacatcacagaag    2460
aaattggccttgtaagtttcatgtgaccctgtggtacagtatgtgtggcaattttgccca    2520
tcacggattttttttattggtatttgcatctgattataaaactaatgcatgatcattgc    2580
aaaaaatgtagataaagaagagcaaatgaaaataaagatttcccccaccgttccacca    2640
cccagaaataatcatggtttaaatgttaatatacaaccttacaattgttttctatataaa    2700
tgaaaacatagatttctttatttcattattttccataaaaatggatcatgtttatgtca    2760
tgtttggctaatggcaagaccctggcacccagtctgggctcaaattctgcctcattgtta    2820
cttagccctgtgacattgggtaaattacacttttttttttttttttttgagacgggg      2880
```

FIG. 1A

```
tctcgctctgtcgcccaggctggagtgcagtggcacgatctcggctcactgcaagtccgc     2940
ctcctgggttcacgccattcttctgcctcagcctcccgagtagctgggactacaggcgcc     3000
tgccaccacgcctggctctttttttttttttttttttttttagtacagacggggtttcac     3060
catgttagccagggtggtctcaatctcctgacctcgtgattcgcccgcctcagcctccca     3120
aagtgctggtgtgagccaccgtgcccagccttactttttttttttgagagggggtctcact   3180
ctgtcacccaggttggagtgcagtggcgcgatctctgctcagtgcaaactccacctcccg     3240
ggtttaagcagttctcctgtcgtagtctcctgagtagctgggattacaggcacaccacca     3300
cggccagctaattttgtattttcagtagagacgggtttcaccatgttgcccaagctggt      3360
ctcgaactcctggcctcaagtgatctgcccgccttggcctcccagagtgctgggattaca     3420
ggtgtgagccaccgcacccggcctcttttttctttttagtctatcataccttgcaaata     3480
cagtggttcttcctatgtgttggttttgatatttatgtaatcaaacacatcagttttttcc   3540
tttctgatttctgactttggggtcatgctgagaaagtcctttcctacctgaagataatac     3600
agtatatacgtttcttactagtattttgtggattttaaaatatttaaatctttagtcc      3660
atctgaacttgttcttctatcagaaatgccacatttaataaataataagtcccatggtat    3720
cagatggctggaaggacctctttcgaaactttgttaattccattaatctgtgtattctt     3780
attctaatgctaatagttccacactagcttcctttatcttttttttctttttttttttt     3840
ttttgagctggagtttcgctcttgttgcccaggctggagtacaatgtcacgatctcggtt    3900
caccgcaacctccgcctcccaggttcaagcaattctcctgcctcatcctcgcgagtagct    3960
ggaattacaggcatgcgccaccacgcctagctattttgtattttagtagagatggggtt   4020
tctccatgttggtcaggctggtctcaaactcccagcctcaggtgatctgcctgcctcggc    4080
ctcccaaaatgctgttattacaggcgtgagccaccacgcccagccttcatcttttaatga    4140
atgtacatgtatgtaatcttttaggtgaacttttttgtaatgttgtgccaagttccttaaa   4200
aagccctttggaagctgggcaggtggccacgcctgtaatcccagcattttgggagtctg     4260
aggcaggtggatcacttgaggccaggagttcaagactagcctagccaaaatgcaaaaccc    4320
tgtctctactaaagatacaaaaattagccggatgcgatggcacatgcctgtaatctcagc    4380
tactcgggaggctgaggtagaagaatcgcttgaaccggggaggcagaggttgcagtgagc    4440
aagatggcgccactgcactccagcctgggtgacagagggagactccatctcaaaaaaaa    4500
aaaaaaaaaaagataaaaggaaacctaagtactcttgggctttgttaaggatttttgtt     4560
aaatatacaaaggattgcagggaaaattaacttattttttaatattgagtatgcttatcca    4620
agagcaaaataatatttctccatttattcaaatcatttaggagcatcatagttttaacat    4680
atgggccttgcacgtatcttaaatttatctctaggcattttaggttgttcagttgttctt    4740
gtgaatgggatctttttctccaaataggattattgttgatatctgttgattatgttaact     4800
ttgtagtttctgactttactgaactgtcttcttagatctaatactcttttcaatttcatc     4860
atatatttctcattcctatttgtttggggttttagggcgggaatattaacgggataag     4920
agagacaaaagaaaatctggaaaaacaattcattttaccttacattgcttgtgattacta    4980
ccacactattactgggttggaaaaaattgtgaaatcccaaggtgcctaataaatgggagg    5040
tacctaagtgttcatttaatgaattgtaatgattattggaatttctctttcagtgagaag    5100
ctcttcatggagatggcagagctcatggtctcagaaggctggaaggatgcaggttatgag    5160
tacctctgcattgatgactgttggatggctccccaaagagattcagaaggcagacttcag    5220
gcagaccctcagcgcttcctcatgggattcgccagctagctaattatgtgagtttatag     5280
ataatgttcttgttcattcagaggactgtaagcacttctgtacagaagcttgtttagaaa    5340
cagccctcatggccgggcgtggtggctcacgctgtaatcccaacactttgggaggccgag    5400
gcgggtggatcacctgaggtcaagagttcaagaccagcctggccaacatggtgaaacccc    5460
aactctattaaaagtacaaaaaattagctgggcatggtggtgaacgcctgtaaccccagc    5520
tacttgggaggctgaggcaggagaatcgcttgaacccaggaggtggaagtttcagtgagc    5580
tgagatcacgccattgcactctagcctgggcaacaaaagagaaactccatctcaaaaaaa    5640
aaaacaaggaaaaaagaaacagccctcatgacacttagaaagtagaatagctggctgtt    5700
atctgaacattgaattgtaaggcttatcaggtggactttgcattccatcagcagacaatt    5760
```

FIG. 1B

```
tttttttttttttttttttgagatggagtctcattctgtctcccaggctggagggcagtg      5820
gtgcgatctcggctcactgcaagctccacctcctgggttcatgccattctcctgcctcag      5880
cctcccaagtagctgggaccacaggcacccgccaccatgcccagttaattttttgtattt      5940
ttagtagagacggggtttcaccatgttagccaagatggtctcgatctcctgacctcgtga      6000
tccgcccacctcggcctcccaaagtgctgggattacaggcatgagccaccgcgcctagcc      6060
tacaaatgttttgtaatagctcttgaggcccatcttggagttctccttttgctaaaacca      6120
ctgaactctctaggaggaaaaaggaacttggttcttgacatatgtgtgcatgtatttcca      6180
tataacctttaggaagctattgcaatggtactataaactagaattttagaagatagaagg      6240
aaaatattctggagatcattgaagagaaatggagtccaacactagttaaagatgatgaag      6300
acagattttttttttgacggagtctcgctctgtcgcccaggctggagtgcagtggcaca      6360
atctcagctcactgcaaccctccacctcttgggttcaagtgattctcctgcctcagcctc      6420
ccaagtagctgggactacaggcgcacaccaccacgcccggctaattttgtattttagt      6480
agagacaaggtttcaccatattcgccaggctggtctcgaactcctgaccttgtaatccgc      6540
ccaccttggcctcccaaagtgctgggattacaggcatgagccaccacgcccggccgatga      6600
agacagattttattcagtactaccacagtagaggaaagagccaagttcaattccaaatac      6660
aacaaagacaggtggagatttatagccaatgagcagattgaggggtcagtggatggaat      6720
atttaagaagacatcaagggtagggagcttcttgctaaagcttcatgtacttaaacaaga      6780
agggtgggggatgagggaaattgatcagatatcaatggtggcagtattgacttagcagga      6840
ttcttgctaagaggtcttgctaggacagacataggaagccaaggtggaggtctagtcgaa      6900
aagaaggctcatcagagaagtctaactaaagtttggtcaagaagagtctttgtcaaggta      6960
aatctatcatttccctcaaaaggtaattttcaggatcccatcaggaagattagcatggct      7020
gctagctttctcctcagttctgggctatagctcacatgcctagtttgaactagctcagca      7080
gaactgggggatttattctttgtcttccaacaaactcatctggatgattttgggggtttg      7140
tggggaaaagccccccaatacctggtgaagtaaccttgtctcttccccagcctggaatgg      7200
ttctctctttctgctacctcacgattgtgcttctacaatggtgactcttttcctccctct      7260
catttcaggttcacagcaaaggactgaagctagggatttatgcagatgttggaaataaaa      7320
cctgcgcaggcttccctgggagttttggatactacgacattgatgcccagacctttgctg      7380
actggggagtagatctgctaaaatttgatggttgttactgtgacagtttggaaaatttgg      7440
cagatggtaatgtttcattccagagatttagccacaaaggaaagaactttgaggccatgg      7500
tagctgagccaaagaaccaatcttcagaattttaaatacctgtcacaatactggaaata      7560
attattctccatgtgccagagctcccatctcttctctttcagttcattaattaattaatt      7620
aattcatgtaaaatccatgcatacctaaccatagctaatattgtgcacttataattcaag      7680
agggctctaagagttaattagtaattgtaactctctataacatcatttaggggagtccag      7740
gttgtcaatcggtcacagagaaagaagcatcttcattcctgccttttcctcaatatacaca      7800
ccatctctgcactacttcctcagaacaatcccagcagtctgggaggtactttacacaatt      7860
taagcacagagcaactgcctgtccctgctgctagtttaaacatgaaccttccaggtagcc      7920
tcttcttaaaatatacagccccagctgggcatgatggctcatgcctgtaatcctagcact      7980
ttgggaggctgaggcgggtggattacttgaggtcaggagttcgagaccaccctggccaac      8040
atggtgaaaccccatctctagtaaaaatacaaaaattagctgactttggtggcacatgcc      8100
tgtaatcccagctacttgggaagctgagacagaagagtcacttgaacctgggaaacagag      8160
gttgcagtgagccaagatcgcaccactgcactccaccctggatgacagactgaacccat      8220
ctcaaaaaattaaataaataaataaactatatatagccccagctggaaatt      8280
catttctttcccttatttacccattgttttctcatacaggttataagcacatgtccttg      8340
gccctgaataggactggcagaagcattgtgtactcctgtgagtggcctctttatatgtgg      8400
cccttcaaaggtgagatagtgagcccagaatccaatagaactgtactgatagatagaa      8460
cttgacaacaaaggaaaccaaggtctccttcaaagtccaacgttacttactatcatccta      8520
ccatctctcccaggttccaaccacttctcaccatcccactgctgtaattatagcctaag      8580
ctaccatcacctggaaagtcatccttgtgtcttcccctttatttcaccattcatgtcctg      8640
```

FIG. 1C

```
tctatcaacagtccttccaccagtatctctaaaatatctcctgaatcagcccacttcctt    8700
ccatcttcactacatgcaccctggccttccaagctactatcggctctcaaccagactgct    8760
gggaccacctgatctctctgcttccactctgtctcaaccccatctattttccaagcagc    8820
actagagttatcatattaaaatgtaaatatcagttttttttttaaagaaaaaaaccctga    8880
gacttaacagagttataaaaaatataaatgtcatcatcagttccctgcttaaaacccta    8940
actcgcttccaattgcacttggaatgaaaccaaactgcactgatccagccttgcctgcc    9000
tccccaaagtccaaggggtcatggctctttcctggctacactggttttctttctgtccc    9060
tcaacactgcaagcctattgctgccccagggcctttacacttgcttttttctgcctaga    9120
acagttcttccccaaagattttaaagggccgggctccttaacattgaagtcgcagacca    9180
aacgccacatatgcagacagttcttctctaactactttaaaatagccctctgtccattca    9240
ttcttcatcacattaacctgtttaattttcttcagagctccacactatttggaagtat    9300
ttgttgacttgttaccatgtctccccactagagtgtaagtttcatgagggcagggacctt    9360
gtctgactttgactgtatctctcgcatatggttaagtgttaaatagttatttatggaatg    9420
aatccctattattccctcattatctctgcaaaatagtctttttctcaacatcttaaacc    9480
tgatatcccacctgcctatctacaaacttttttttgcgacagagtctcactgtcaccca    9540
ggctagagtgcagtggcgccatctcggctcactgcaacctccgcctcccgggtttaagcg    9600
attctcttgcctcagcctcccagtagctgggattataggcgtgcgctaccacatctggct    9660
aattttgtatttagtagagatggtttcaccatgttggccaggcttgtctcgaactcc    9720
tgacctcagatgatccacctgcctcggcctcccaaagtgctgggattacaggcatgagcc    9780
accgtgcccagcctctacaaacttttattccattaacaaactatatgctgggatttaag    9840
ttttcttaatacttgatggagtcctatgtaattttcgagcttttaattttactaagacca    9900
ttttagttctgattatagaagtaaattaactttaagggatttcaagttatatggcctact    9960
tctgaagcaaacttcttacagtgaaaattcattataagggtttagacctccttatggaga   10020
cgttcaatctgtaaactcaagagaaggctacaagtgcctcctttaaactgttttcatctc   10080
acaaggatgttagtagaaagtaaacagaagagtcatatctgttttcacagcccaattata   10140
cagaaatccgacagtactgcaatcactggcgaaattttgctgacattgatgattcctgga   10200
aaagtataaagagtatcttggactggacatcttttaaccaggagagaattgttgatgttg   10260
ctggaccagggggttggaatgacccagatatggtaaaaacttgagccctccttgttcaag   10320
accctgcggtaggcttgtttcctattttgacattcaaggtaaatacaggtaaagttcctg   10380
ggaggaggctttatgtgagagtacttagagcaggatgctgtggaaagtggtttctccata   10440
tgggtcatctaggtaactttaagaatgtttcctcctctcttgtttgaattatttcattct   10500
ttttctcagttagtgattggcaactttggcctcagctggaatcagcaagtaactcagatg   10560
gccctctgggctatcatggctgctcctttattcatgtctaatgacctccgacacatcagc   10620
cctcaagccaaagctctccttcaggataaggacgtaattgccatcaatcaggacccctttg   10680
ggcaagcaagggtaccagcttagacaggtaaataagagtatataatttaagatggcttta   10740
tatcccaataccaactttgtcttgggcctaaatctattttttcccttgctcttgatgt    10800
tactatcagtaataaagcttcttgctagaaacattactttatttccaaaataatgctaca   10860
ggatcattttaattttcctacaagtgcttgatagttctgacattaagaatgaatgccaa    10920
actaacagggccacttatcactagttgctaagcaaccacactttcttggtttttcaggga    10980
gacaactttgaagtgtgggaacgacctctctcaggcttagcctgggctgtagctatgata    11040
aaccggcaggagattggtggacctcgctcttataccatcgcagttgcttccctgggtaaa    11100
ggagtggcctgtaatcctgcctgcttcatcacacagctcctcctgtgaaaaggaagcta    11160
gggttctatgaatggacttcaaggttaagaagtcacataaatcccacaggcactgttttg    11220
cttcagctagaaaatacaatgcagatgtcattaaaagacttactttaaaatgtttattt    11280
attgccaactactacttcctgtccaccttttctccattcactttaaaagctcaaggcta   11340
ggtggctcatgcctgtaatcccagcactttgggaggctgaggcgggcagatcacctgagg   11400
tcgggactttgagacccgcctggacaacatggtgaaaccccatttctaataaaaatataa   11460
aaattagccaggtgtggtggcgcacctgtggtcccagctactctggggctgaggcatga   11520
```

FIG. 1D

```
gaatcgcttgaacccgggagtggaggttgcattgagctgagatcatgccacctcactcca    11580
gcctgggcaacaaagattccatctcaaaaaaaaaaaaaagccaggcacagtggctcatg    11640
cctggaatcccagcacttttggaagctgaggcaggcagatcacttgaggttaggatttca    11700
agaccagcctggctaacatagtaaagccctgtctctactaaaaatacaaaaattagccag    11760
gtatggtggcgagcttctgtagccccagctactcaggagactgaggcaggagaatcactt    11820
gaacccgggaagtgggggggtgcagtgacccaagatcacgccactgcattccagcctggg    11880
caacagagcaagactccatctcaaaaaaaaagttctatttccttgaataaaattttccg    11940
aagtttaaactttaggaataaaactattaaacccgtatttactcatccagatacccaccc    12000
cccttgttgagattctctcccaattatcaaaatgtgtagcatatttaactaccaagagct    12060
aaacatcattaagactgaaatgtattaagaaggatgtataggccaggcacggtgtctcac    12120
gcctgtaatcccaacactttgggaggccaagtcgggcggatcacgaggtcaggagatgga    12180
gaccatcctggccaacatggtgaaaccccctctctactaaaaatacaaaaattagccagg    12240
caggtggcaggcacctgtaatcccagctactccagaggctgaggcaggacaatcacttga    12300
acctgggaggcagaggctgcagtgagctgaggttgtaccaattgcactccagcctaggta    12360
acgagcaacactccatctcaaaaaagaaaaaaaaaagatgtataatttggaactgtta    12420
agaggcattttaaaga                                                12436
```

FIG. 1E

```
MQLRNPELHL GCALALRFLA LVSWDIPGAR ALDNGLARTP TMGWLHWERF MCNLDCQEEP   60
DSCISEKLFM EMAELMVSEG WKDAGYEYLC IDDCWMAPQR DSEGRLQADP QRFPHGIRQL  120
ANYVHSKGLK LGIYADVGNK TCAGFPGSFG YYDIDAQTFA DWGVDLLKFD GCYCDSLENL  180
ADGYKHMSLA LNRTGRSIVY SCEWPLYMWP FQKPNYTEIR QYCNHWRNFA DIDDSWKSIK  240
SILDWTSFNQ ERIVDVAGPG GWNDPDMLVI GNFGLSWNQQ VTQMALWAIM AAPLFMSNDL  300
RHISPQAKAL LQDKDVIAIN QDPLGKQGYQ LRQGDNFEVW ERPLSGLAWA VAMINRQEIG  360
GPRSYTIAVA SLGKGVACNP ACFITQLLPV KRKLGFYEWT SRLRSHINPT GTVLLQLENT  420
MQMSLKDLL                                                         429
```

FIG. 2

TREATMENT OF FABRY DISEASE IN ERT-NAÏVE AND ERT-EXPERIENCED PATIENTS

CROSS-REFERENCE TO RELATED APPLICATIONS

This application is the National Stage entry of PCT/US17/42872, filed on Jul. 19, 2017, which claims priority to U.S. application Ser. No. 15/213,920, filed on Jul. 19, 2016, which are incorporated herein by reference in their entireties.

TECHNICAL FIELD

Principles and embodiments of the present invention relate generally to the use of pharmacological chaperones for the treatment of lysosomal storage disorders, particularly the use of migalastat for the treatment of Fabry disease.

BACKGROUND

Fabry disease is a progressive, X-linked inborn error of glycosphingolipid metabolism caused by a deficiency in the lysosomal enzyme α-galactosidase A (α-Gal A) as a result of mutations in the α-Gal A gene (GLA). Despite being an X-linked disorder, females can express varying degrees of clinical manifestations. Fabry is a rare disease with incidence estimated between 1 in 40,000 males to 1 in 117,000 in the general population. Moreover, there are variants of later onset phenotype of Fabry disease that can be under-diagnosed, as they do not present with classical signs and symptoms. This, and newborn screening for Fabry disease, suggests that the actual incidence of Fabry disease can be higher than currently estimated.

Untreated, life expectancy in Fabry patients is reduced and death usually occurs in the fourth or fifth decade because of vascular disease affecting the kidneys, heart and/or central nervous system. The enzyme deficiency leads to intracellular accumulation of the substrate, globotriaosylceramide (GL-3) in the vascular endothelium and visceral tissues throughout the body. Gradual deterioration of renal function and the development of azotemia, due to glycosphingolipid deposition, usually occur in the third to fifth decades of life, but can occur as early as in the second decade. Renal lesions are found in both hemizygous (male) and heterozygous (female) patients.

Cardiac disease as a result of Fabry disease occurs in most males and many females. Early cardiac findings include left ventricular enlargement, valvular involvement and conduction abnormalities. Mitral insufficiency is the most frequent valvular lesion typically present in childhood or adolescence. Cerebrovascular manifestations result primarily from multifocal small-vessel involvement and can include thromboses, transient ischemic attacks, basilar artery ischemia and aneurysm, seizures, hemiplegia, hemianesthesia, aphasia, labyrinthine disorders, or cerebral hemorrhages. Average age of onset of cerebrovascular manifestations is 33.8 years. Personality change and psychotic behavior can manifest with increasing age.

The current FDA-approved treatment for Fabry disease is enzyme replacement therapy (ERT). Two α-Gal A products are currently available for the treatment of Fabry disease: agalsidase alfa (Replagal®, Shire Human Genetic Therapies) and agalsidase beta (Fabrazyme®; Genzyme Corporation). These two forms of ERT are intended to compensate for a patient's inadequate α-Gal A activity with a recombinant form of the enzyme, administered intravenously. While ERT is effective in many settings, the treatment also has limitations. ERT has not been demonstrated to decrease the risk of stroke, cardiac muscle responds slowly, and GL-3 elimination from some of the cell types of the kidneys is limited. Some patients also develop immune reactions to ERT.

Accordingly, there remains a need for therapies for the treatment of Fabry disease.

SUMMARY

Various aspects of the present invention relate to the treatment of Fabry disease in ERT-naïve and ERT-experienced patients using migalastat.

One aspect of the present invention pertains to a method of reducing left ventricular mass index (LVMi) in an ERT-experienced patient having Fabry disease, the method comprising administering to the patient a formulation comprising an effective amount of migalastat or salt thereof every other day, wherein the effective amount is about 123 mg free base equivalent (FBE).

In one or more embodiments, the patient has left ventricular hypertrophy (LVH) prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

In one or more embodiments, the administration of migalastat or a salt thereof provides an average decrease of LVMi in a group of ERT-experienced patients of at least about 5 g/m² after 18 months of administration of migalastat or a salt thereof. In one or more embodiments, the administration of migalastat or a salt thereof provides an average decrease of LVMi in a group of ERT-experienced patients of about 6.6 g/m² after 18 months of administration of migalastat or a salt thereof.

In one or more embodiments, the administration of migalastat or a salt thereof provides an average decrease of LVMi in a group of ERT-experienced patients of at least about 2 g/m² after 30 months of administration of migalastat or a salt thereof. In one or more embodiments, the administration of migalastat or a salt thereof provides an average decrease of LVMi in a group of ERT-experienced patients of about 3.8 g/m² after 30 months of administration of migalastat or a salt thereof.

In one or more embodiments, the administration of migalastat or a salt thereof provides an average decrease of LVMi in a group of ERT-experienced patients with LVH of at least about 5 g/m² after 30 months of administration of migalastat or a salt thereof. In one or more embodiments, the administration of migalastat or a salt thereof provides an average decrease of LVMi in a group of ERT-experienced patients with LVH of about 9 g/m² after 30 months of administration of migalastat or a salt thereof.

Another aspect of the present invention pertains to a method of reducing LVMi in an ERT-naïve patient having Fabry disease, the method comprising administering to the patient a formulation comprising an effective amount of migalastat or salt thereof every other day, wherein the effective amount is about 123 mg FBE.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

In one or more embodiments, the administration of migalastat or a salt thereof provides an average decrease of LVMi in a group of ERT-naïve patients of at least about 5 $g/m^2$ after 18 to 24 months of administration of migalastat or a salt thereof. In one or more embodiments, the administration of migalastat or a salt thereof provides an average decrease of LVMi in a group of ERT-naïve patients of about 7.7 $g/m^2$ after 18 to 24 months of administration of migalastat or a salt thereof.

In one or more embodiments, the administration of migalastat or a salt thereof provides an average decrease of LVMi in a group of ERT-naïve patients of at least about 10 $g/m^2$ after 30 to 36 months of administration of migalastat or a salt thereof. In one or more embodiments, the administration of migalastat or a salt thereof provides an average decrease of LVMi in a group of ERT-naïve patients of about 17 $g/m^2$ after 30 to 36 months of administration of migalastat or a salt thereof.

In one or more embodiments, the administration of migalastat or a salt thereof provides an average decrease of LVMi in a group of ERT-experienced patients with LVH of at least about 15 $g/m^2$ after 30 to 36 months of administration of migalastat or a salt thereof. In one or more embodiments, the administration of migalastat or a salt thereof provides an average decrease of LVMi in a group of ERT-naïve patients with LVH of about 20.8 $g/m^2$ after 30 to 36 months of administration of migalastat or a salt thereof.

Another aspect of the present invention pertains to a method of normalizing LVMi in a patient having Fabry disease, the method comprising administering to the patient a formulation comprising an effective amount of migalastat or salt thereof every other day, wherein the effective amount is about 123 mg FBE.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

Another aspect of the present invention pertains to a method of normalizing LVMi in an ERT-experienced patient having Fabry disease, the method comprising administering to the patient a formulation comprising an effective amount of migalastat or salt thereof every other day, wherein the effective amount is about 123 mg FBE.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

In one or more embodiments, the administration of migalastat or a salt thereof provides an average decrease of LVMi in a group of ERT-experienced patients of at least about 5 $g/m^2$ after 18 months of administration of migalastat or a salt thereof. In one or more embodiments, the administration of migalastat or a salt thereof provides an average decrease of LVMi in a group of ERT-experienced patients of about 6.6 $g/m^2$ after 18 months of administration of migalastat or a salt thereof.

In one or more embodiments, the administration of migalastat or a salt thereof provides an average decrease of LVMi in a group of ERT-experienced patients of at least about 2 $g/m^2$ after 30 months of administration of migalastat or a salt thereof. In one or more embodiments, the administration of migalastat or a salt thereof provides an average decrease of LVMi in a group of ERT-experienced patients of about 3.8 $g/m^2$ after 30 months of administration of migalastat or a salt thereof.

In one or more embodiments, the administration of migalastat or a salt thereof provides an average decrease of LVMi in a group of ERT-experienced patients with LVH of at least about 5 $g/m^2$ after 30 months of administration of migalastat or a salt thereof. In one or more embodiments, the administration of migalastat or a salt thereof provides an average decrease of LVMi in a group of ERT-experienced patients with LVH of about 9 $g/m^2$ after 30 months of administration of migalastat or a salt thereof.

Another aspect of the present invention pertains to a method of normalizing LVMi in an ERT-naïve patient having Fabry disease, the method comprising administering to the patient a formulation comprising an effective amount of migalastat or salt thereof every other day, wherein the effective amount is about 123 mg FBE.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, wherein the migalastat or salt thereof is administered for at least 30 months.

In one or more embodiments, the administration of migalastat or a salt thereof provides an average decrease of LVMi in a group of ERT-naïve patients of at least about 5 g/m² after 18 to 24 months of administration of migalastat or a salt thereof. In one or more embodiments, the administration of migalastat or a salt thereof provides an average decrease of LVMi in a group of ERT-naïve patients of about 7.7 g/m² after 18 to 24 months of administration of migalastat or a salt thereof.

In one or more embodiments, the administration of migalastat or a salt thereof provides an average decrease of LVMi in a group of ERT-naïve patients of at least about 10 g/m² after 30 to 36 months of administration of migalastat or a salt thereof. In one or more embodiments, the administration of migalastat or a salt thereof provides an average decrease of LVMi in a group of ERT-naïve patients of about 17 g/m² after 30 to 36 months of administration of migalastat or a salt thereof.

In one or more embodiments, the administration of migalastat or a salt thereof provides an average decrease of LVMi in a group of ERT-naïve patients with LVH of at least about 15 g/m² after 30 to 36 months of administration of migalastat or a salt thereof. In one or more embodiments, the administration of migalastat or a salt thereof provides an average decrease of LVMi in a group of ERT-naïve patients with LVH of about 20.8 g/m² after 30 to 36 months of administration of migalastat or a salt thereof.

Another aspect of the present invention pertains to a method of reducing podocyte GL-3 in a patient having Fabry disease, the method comprising administering to the patient a formulation comprising an effective amount of migalastat or salt thereof every other day, wherein the effective amount is about 123 mg FBE.

In one or more embodiments, the migalastat or salt thereof enhances α α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 6 months.

In one or more embodiments, the patient is an ERT-naïve patient.

In one or more embodiments, the patient is an ERT-experienced patient.

Another aspect of the present invention pertains to a method of reducing podocyte volume in a patient having Fabry disease, the method comprising administering to the patient a formulation comprising an effective amount of migalastat or salt thereof every other day, wherein the effective amount is about 123 mg FBE.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 6 months.

In one or more embodiments, the administration of migalastat or a salt thereof provides an average reduction of podocyte volume in a group of ERT-naive patients of at least about 30% after 6 months of administration of migalastat or a salt thereof.

In one or more embodiments, the administration of migalastat or a salt thereof provides an average reduction of podocyte volume in a group of ERT-naive patients of about 47% after 6 months of administration of migalastat or a salt thereof.

In one or more embodiments, the patient is an ERT-naïve patient.

In one or more embodiments, the patient is an ERT-experienced patient.

Another aspect of the present invention pertains to a method of reducing GL-3 inclusion volume per podocyte in a patient having Fabry disease, the method comprising administering to the patient a formulation comprising an effective amount of migalastat or salt thereof every other day, wherein the effective amount is about 123 mg FBE.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 6 months.

In one or more embodiments, the administration of migalastat or a salt thereof provides an average reduction of GL-3 inclusion volume per podocyte in a group of ERT-naive patients of at least about 30% after 6 months of administration of migalastat or a salt thereof.

In one or more embodiments, the administration of migalastat or a salt thereof provides an average reduction of GL-3 inclusion volume per podocyte in a group of ERT-naive patients of about 50% after 6 months of administration of migalastat or a salt thereof.

In one or more embodiments, the patient is an ERT-naïve patient.

In one or more embodiments, the patient is an ERT-experienced patient.

Another aspect of the present invention pertains to a method of treating Fabry disease in an ERT-experienced patient, the method comprising administering to the patient a formulation comprising an effective amount of migalastat or salt thereof every other day, wherein the effective amount is about 123 mg FBE and wherein administering the formulation reduces the patient's left ventricular mass (LVM).

In one or more embodiments, the patient has left ventricular hypertrophy (LVH) prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

In one or more embodiments, the administration of migalastat or a salt thereof provides an average decrease of LVMi in a group of ERT-experienced patients of at least about 5 g/m$^2$ after 18 months of administration of migalastat or a salt thereof. In one or more embodiments, the administration of migalastat or a salt thereof provides an average decrease of LVMi in a group of ERT-experienced patients of about 6.6 g/m$^2$ after 18 months of administration of migalastat or a salt thereof.

In one or more embodiments, the administration of migalastat or a salt thereof provides an average decrease of LVMi in a group of ERT-experienced patients of at least about 2 g/m$^2$ after 30 months of administration of migalastat or a salt thereof. In one or more embodiments, the administration of migalastat or a salt thereof provides an average decrease of LVMi in a group of ERT-experienced patients of about 3.8 g/m$^2$ after 30 months of administration of migalastat or a salt thereof.

In one or more embodiments, the administration of migalastat or a salt thereof provides an average decrease of LVMi in a group of ERT-experienced patients with LVH of at least about 5 g/m$^2$ after 30 months of administration of migalastat or a salt thereof. In one or more embodiments, the administration of migalastat or a salt thereof provides an average decrease of LVMi in a group of ERT-experienced patients with LVH of about 9 g/m$^2$ after 30 months of administration of migalastat or a salt thereof.

Another aspect of the present invention pertains to a method of treating Fabry disease in an ERT-naïve patient, the method comprising administering to the patient a formulation comprising an effective amount of migalastat or salt thereof every other day, wherein the effective amount is about 123 mg FBE and wherein administering the formulation reduces the patient's LVM.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

In one or more embodiments, the administration of migalastat or a salt thereof provides an average decrease of LVMi in a group of ERT-naïve patients of at least about 5 g/m$^2$ after 18 to 24 months of administration of migalastat or a salt thereof. In one or more embodiments, the administration of migalastat or a salt thereof provides an average decrease of LVMi in a group of ERT-naïve patients of about 7.7 g/m$^2$ after 18 to 24 months of administration of migalastat or a salt thereof.

In one or more embodiments, the administration of migalastat or a salt thereof provides an average decrease of LVMi in a group of ERT-naïve patients of at least about 10 g/m$^2$ after 30 to 36 months of administration of migalastat or a salt thereof. In one or more embodiments, the administration of migalastat or a salt thereof provides an average decrease of LVMi in a group of ERT-naïve patients of about 17 g/m$^2$ after 30 to 36 months of administration of migalastat or a salt thereof.

In one or more embodiments, the administration of migalastat or a salt thereof provides an average decrease of LVMi in a group of ERT-experienced patients with LVH of at least about 15 g/m$^2$ after 30 to 36 months of administration of migalastat or a salt thereof. In one or more embodiments, the administration of migalastat or a salt thereof provides an average decrease of LVMi in a group of ERT-naïve patients with LVH of about 20.8 g/m$^2$ after 30 to 36 months of administration of migalastat or a salt thereof.

Another aspect of the present invention pertains to a method of treating Fabry disease, the method comprising administering to a patient in need a formulation comprising an effective amount of migalastat or salt thereof every other day, wherein the effective amount is about 123 mg FBE and wherein administering the formulation normalizes the patient's LVMi.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

Another aspect of the present invention pertains to a method of treating Fabry disease in an ERT-experienced patient, the method comprising administering to the patient a formulation comprising an effective amount of migalastat or salt thereof every other day, wherein the effective amount is about 123 mg FBE and wherein administering the formulation normalizes the patient's LVMi.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, the migalastat or salt thereof is administered for at least 30 months.

In one or more embodiments, the administration of migalastat or a salt thereof provides an average decrease of LVMi in a group of ERT-experienced patients of at least about 5 g/m$^2$ after 18 months of administration of migalastat or a salt thereof. In one or more embodiments, the administration of migalastat or a salt thereof provides an average decrease of LVMi in a group of ERT-experienced patients of about 6.6 g/m$^2$ after 18 months of administration of migalastat or a salt thereof.

In one or more embodiments, the administration of migalastat or a salt thereof provides an average decrease of LVMi in a group of ERT-experienced patients of at least about 2 g/m² after 30 months of administration of migalastat or a salt thereof. In one or more embodiments, the administration of migalastat or a salt thereof provides an average decrease of LVMi in a group of ERT-experienced patients of about 3.8 g/m² after 30 months of administration of migalastat or a salt thereof.

In one or more embodiments, the administration of migalastat or a salt thereof provides an average decrease of LVMi in a group of ERT-experienced patients with LVH of at least about 5 g/m² after 30 months of administration of migalastat or a salt thereof. In one or more embodiments, the administration of migalastat or a salt thereof provides an average decrease of LVMi in a group of ERT-experienced patients with LVH of about 9 g/m² after 30 months of administration of migalastat or a salt thereof.

Another aspect of the present invention pertains to a method of treating Fabry disease in an ERT-naïve patient, the method comprising administering to the patient a formulation comprising an effective amount of migalastat or salt thereof every other day, wherein the effective amount is about 123 mg FBE and wherein administering the formulation normalizes the patient's LVMi.

In one or more embodiments, the patient has LVH prior to initiating administration of the migalastat or salt thereof.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 18 months.

In one or more embodiments, wherein the migalastat or salt thereof is administered for at least 30 months.

In one or more embodiments, the administration of migalastat or a salt thereof provides an average decrease of LVMi in a group of ERT-naïve patients of at least about 5 g/m² after 18 to 24 months of administration of migalastat or a salt thereof. In one or more embodiments, the administration of migalastat or a salt thereof provides an average decrease of LVMi in a group of ERT-naïve patients of about 7.7 g/m² after 18 to 24 months of administration of migalastat or a salt thereof.

In one or more embodiments, the administration of migalastat or a salt thereof provides an average decrease of LVMi in a group of ERT-naïve patients of at least about 10 g/m² after 30 to 36 months of administration of migalastat or a salt thereof. In one or more embodiments, the administration of migalastat or a salt thereof provides an average decrease of LVMi in a group of ERT-naïve patients of about 17 g/m² after 30 to 36 months of administration of migalastat or a salt thereof.

In one or more embodiments, the administration of migalastat or a salt thereof provides an average decrease of LVMi in a group of ERT-naïve patients with LVH of at least about 15 g/m² after 30 to 36 months of administration of migalastat or a salt thereof. In one or more embodiments, the administration of migalastat or a salt thereof provides an average decrease of LVMi in a group of ERT-naïve patients with LVH of about 20.8 g/m² after 30 to 36 months of administration of migalastat or a salt thereof.

Another aspect of the present invention pertains to a method of treating Fabry disease, the method comprising administering to a patient in need a formulation comprising an effective amount of migalastat or salt thereof every other day, wherein the effective amount is about 123 mg FBE and wherein administering the formulation reduces podocyte GL-3 in the patient.

In one or more embodiments, the migalastat or salt thereof enhances α α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 6 months.

In one or more embodiments, the patient is an ERT-naïve patient.

In one or more embodiments, the patient is an ERT-experienced patient.

Another aspect of the present invention pertains to a method of treating Fabry disease, the method comprising administering to a patient in need a formulation comprising an effective amount of migalastat or salt thereof every other day, wherein the effective amount is about 123 mg FBE and wherein administering the formulation reduces podocyte volume in the patient.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 6 months.

In one or more embodiments, the administration of migalastat or a salt thereof provides an average reduction of podocyte volume in a group of ERT-naive patients of at least about 30% after 6 months of administration of migalastat or a salt thereof.

In one or more embodiments, the administration of migalastat or a salt thereof provides an average reduction of podocyte volume in a group of ERT-naive patients of about 47% after 6 months of administration of migalastat or a salt thereof.

In one or more embodiments, the patient is an ERT-naïve patient.

In one or more embodiments, the patient is an ERT-experienced patient.

Another aspect of the present invention pertains to a method of treating Fabry disease, the method comprising administering to a patient in need a formulation comprising an effective amount of migalastat or salt thereof every other day, wherein the effective amount is about 123 mg FBE and wherein administering the formulation reduces GL-3 inclusion volume per podocyte in the patient.

In one or more embodiments, the migalastat or salt thereof enhances α-Gal A activity.

In one or more embodiments, the patient is administered about 123 mg of migalastat free base every other day.

In one or more embodiments, the patient is administered about 150 mg of migalastat hydrochloride every other day.

In one or more embodiments, the formulation comprises an oral dosage form. In one or more embodiments, the oral dosage form comprises a tablet, a capsule or a solution.

In one or more embodiments, the migalastat or salt thereof is administered for at least 6 months.

In one or more embodiments, the administration of migalastat or a salt thereof provides an average reduction of GL-3 inclusion volume per podocyte in a group of ERT-naïve patients of at least about 30% after 6 months of administration of migalastat or a salt thereof.

In one or more embodiments, the administration of migalastat or a salt thereof provides an average reduction of GL-3 inclusion volume per podocyte in a group of ERT-naïve patients of about 50% after 6 months of administration of migalastat or a salt thereof.

In one or more embodiments, the patient is an ERT-naïve patient.

In one or more embodiments, the patient is an ERT-experienced patient.

BRIEF DESCRIPTION OF THE DRAWINGS

Further features of the present invention will become apparent from the following written description and the accompanying figures, in which:

FIGS. 1A-E show the full DNA sequence of the human wild-type GLA gene (SEQ ID NO: 1).

FIG. 2 shows the wild-type α-Gal A protein (SEQ ID NO: 2).

DETAILED DESCRIPTION

Figure 3:
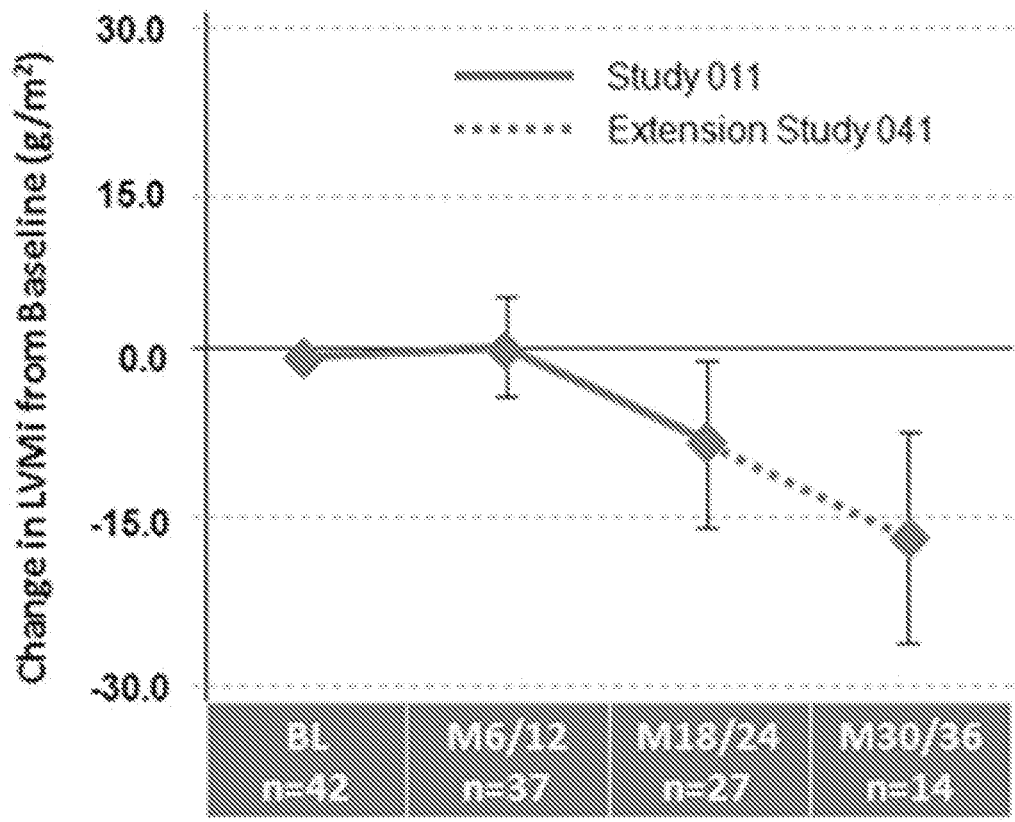
FIG. 3 shows the average LVMi changes from baseline to after 6/12, 18/24 and 30/36 months of migalastat therapy, as described in Example 1.

Before describing several exemplary embodiments of the invention, it is to be understood that the invention is not limited to the details of construction or process steps set forth in the following description. The invention is capable of other embodiments and of being practiced or being carried out in various ways.

Various aspects of the present invention pertain to dosing regimens for the administration of pharmacological chaperones such as migalastat for the treatment of Fabry disease. In one or more embodiments, the dosing regimens of migalastat improve one or more cardiac parameters and/or one or more renal parameters of a patient.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolism due to deficient lysosomal α-Gal A activity. This defect causes accumulation of the substrate globotriaosylceramide ("GL-3", also known as Gb3 or ceramide trihexoside) and related glycosphingolipids in vascular endothelial lysosomes of the heart, kidneys, skin, and other tissues.

The term "atypical Fabry disease" refers to patients with primarily cardiac manifestations of the α-Gal A deficiency, namely progressive GL-3 accumulation in myocardial cells that leads to significant enlargement of the heart, particularly the left ventricle.

A "carrier" is a female who has one X chromosome with a defective α-Gal A gene and one X chromosome with the normal gene and in whom X chromosome inactivation of the normal allele is present in one or more cell types. A carrier is often diagnosed with Fabry disease.

A "patient" refers to a subject who has been diagnosed with or is suspected of having a particular disease. The patient may be human or animal.

A "Fabry patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

The term "ERT-naïve patient" refers to a Fabry patient that has never received ERT or has not received ERT for at least 6 months prior to initiating migalastat therapy.

The term "ERT-experienced patient" refers to a Fabry patient that was receiving ERT immediately prior to initiating migalastat therapy. In some embodiments, the ERT-experienced patient has received at least 12 months of ERT immediately prior to initiating migalastat therapy.

Human α-galactosidase A (α-Gal A) refers to an enzyme encoded by the human GLA gene. The full DNA sequence of α-Gal A, including introns and exons, is available in GenBank Accession No. X14448.1 and shown in SEQ ID NO: 1 and FIGS. 1A-E. The human α-Gal A enzyme consists of 429 amino acids and is available in GenBank Accession Nos. X14448.1 and U78027.1 and shown in SEQ ID NO: 2 and FIG. 2.

The term "mutant protein" includes a protein which has a mutation in the gene encoding the protein which results in the inability of the protein to achieve a stable conformation under the conditions normally present in the endoplasmic reticulum. The failure to achieve a stable conformation results in a substantial amount of the enzyme being degraded, rather than being transported to the lysosome. Such a mutation is sometimes called a "conformational mutant." Such mutations include, but are not limited to, missense mutations, and in-frame small deletions and insertions.

As used herein in one embodiment, the term "mutant α-Gal A" includes an α-Gal A which has a mutation in the gene encoding α-Gal A which results in the inability of the enzyme to achieve a stable conformation under the conditions normally present in the endoplasmic reticulum. The failure to achieve a stable conformation results in a substantial amount of the enzyme being degraded, rather than being transported to the lysosome.

As used herein, the term "pharmacological chaperone" ("PC") refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the endoplasmic reticulum to another cellular location, preferably a native cellular location, i.e., prevents endoplasmic reticulum-associated degradation of the protein; (iii) prevents aggregation of misfolded proteins; and/or (iv) restores or enhances at least partial wild-type function and/or activity to the protein. A compound that specifically binds to e.g., α-Gal A, means that it binds to and exerts a chaperone effect on the enzyme and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones. In one or more embodiments of the present invention, the PC may be a reversible competitive inhibitor.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

As used herein, the term "specifically binds" refers to the interaction of a pharmacological chaperone with a protein such as α-Gal A, specifically, an interaction with amino acid residues of the protein that directly participate in contacting the pharmacological chaperone. A pharmacological chaperone specifically binds a target protein, e.g., α-Gal A, to exert a chaperone effect on the protein and not a generic group of related or unrelated proteins. The amino acid residues of a protein that interact with any given pharmacological chaperone may or may not be within the protein's "active site." Specific binding can be evaluated through routine binding assays or through structural studies, e.g., co-crystallization, NMR, and the like. The active site for α-Gal A is the substrate binding site.

"Deficient α-Gal A activity" refers to α-Gal A activity in cells from a patient which is below the normal range as compared (using the same methods) to the activity in normal individuals not having or suspected of having Fabry or any other disease (especially a blood disease).

As used herein, the terms "enhance α-Gal A activity" or "increase α-Gal A activity" refer to increasing the amount of α-Gal A that adopts a stable conformation in a cell contacted with a pharmacological chaperone specific for the α-Gal A, relative to the amount in a cell (preferably of the same cell-type or the same cell, e.g., at an earlier time) not contacted with the pharmacological chaperone specific for the α-Gal A. This term also refers to increasing the trafficking of α-Gal A to the lysosome in a cell contacted with a pharmacological chaperone specific for the α-Gal A, relative to the trafficking of α-Gal A not contacted with the pharmacological chaperone specific for the protein. These terms refer to both wild-type and mutant α-Gal A. In one embodiment, the increase in the amount of α-Gal A in the cell is measured by measuring the hydrolysis of an artificial substrate in lysates from cells that have been treated with the PC. An increase in hydrolysis is indicative of increased α-Gal A activity.

The term "α-Gal A activity" refers to the normal physiological function of a wild-type α-Gal A in a cell. For example, α-Gal A activity includes hydrolysis of GL-3.

A "responder" is an individual diagnosed with or suspected of having a lysosomal storage disorder, such, for example Fabry disease, whose cells exhibit sufficiently increased α-Gal A activity, respectively, and/or amelioration of symptoms or improvement in surrogate markers, in response to contact with a PC. Non-limiting examples of improvements in surrogate markers for Fabry are lyso-GB3 and those disclosed in U.S. Patent Application Publication No. US 2010/0113517.

Non-limiting examples of improvements in surrogate markers for Fabry disease disclosed in U.S. 2010/0113517 include increases in α-Gal A levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in plasma globotriaosylsphingosine (lyso-Gb3); reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin; the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities). Another type of clinical marker that can be assessed for Fabry disease is the prevalence of deleterious cardiovascular manifestations.

As used herein, the term "normalizing LVMi" refers to reducing the LVMi of a patient from an above-normal range to within the normal range. The normal range of LVMi for a female is 43-95 g/m$^2$ and the normal range of LVMi for a male is 49-115 g/m$^2$. Thus, normalizing LVMi for a female patient is reducing LVMi from >95 g/m$^2$ to within the range of 43-95 g/m$^2$, and normalizing LVMi for a male patient is reducing LVMi from >115 g/m$^2$ to within the range of 49-115 g/m$^2$.

The phrase "pharmaceutically acceptable" refers to molecular entities and compositions that are physiologically tolerable and do not typically produce untoward reactions when administered to a human. In some embodiments, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" in reference to a pharmaceutical carrier refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The term "enzyme replacement therapy" or "ERT" refers to the introduction of a non-native, purified enzyme into an individual having a deficiency in such enzyme. The administered protein can be obtained from natural sources or by recombinant expression (as described in greater detail below). The term also refers to the introduction of a purified enzyme in an individual otherwise requiring or benefiting from administration of a purified enzyme, e.g., suffering from enzyme insufficiency. The introduced enzyme may be a purified, recombinant enzyme produced in vitro, or protein purified from isolated tissue or fluid, such as, e.g., placenta or animal milk, or from plants.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Fabry Disease

Fabry disease is a rare, progressive and devastating X-linked lysosomal storage disorder. Mutations in the GLA gene result in a deficiency of the lysosomal enzyme, α-Gal A, which is required for glycosphingolipid metabolism. Beginning early in life, the reduction in α-Gal A activity results in an accumulation of glycosphingolipids, including GL-3 and plasma lyso-Gb3, and leads to the symptoms and life-limiting sequelae of Fabry disease, including pain, gastrointestinal symptoms, renal failure, cardiomyopathy, cerebrovascular events, and early mortality. Early initiation of therapy and lifelong treatment provide an opportunity to slow disease progression and prolong life expectancy.

Fabry disease encompasses a spectrum of disease severity and age of onset, although it has traditionally been divided into 2 main phenotypes, "classic" and "late-onset". The classic phenotype has been ascribed primarily to males with undetectable to low α-Gal A activity and earlier onset of renal, cardiac and/or cerebrovascular manifestations. The late-onset phenotype has been ascribed primarily to males with higher residual α-Gal A activity and later onset of these disease manifestations. Heterozygous female carriers typically express the late-onset phenotype but depending on the pattern of X-chromosome inactivation may also display the classic phenotype.

More than 800 Fabry disease-causing GLA mutations have been identified. Approximately 60% are missense mutations, resulting in single amino acid substitutions in the α-Gal A enzyme. Missense GLA mutations often result in the production of abnormally folded and unstable forms of α-Gal A and the majority are associated with the classic phenotype. Normal cellular quality control mechanisms in the endoplasmic reticulum block the transit of these abnormal proteins to lysosomes and target them for premature degradation and elimination. Many missense mutant forms are targets for migalastat, an α-Gal A-specific pharmacological chaperone.

The clinical manifestations of Fabry disease span a broad spectrum of severity and roughly correlate with a patient's residual α-Gal A levels. The majority of currently treated patients are referred to as classic Fabry patients, most of whom are males. These patients experience disease of various organs, including the kidneys, heart and brain, with disease symptoms first appearing in adolescence and typically progressing in severity until death in the fourth or fifth decade of life. A number of recent studies suggest that there are a large number of undiagnosed males and females that have a range of Fabry disease symptoms, such as impaired cardiac or renal function and strokes, that usually first appear in adulthood. Individuals with this type of Fabry disease, referred to as later-onset Fabry disease, tend to have higher residual α-Gal A levels than classic Fabry patients. Individuals with later-onset Fabry disease typically first experience disease symptoms in adulthood, and often have disease symptoms focused on a single organ, such as enlargement of the left ventricle or progressive kidney failure. In addition, later-onset Fabry disease may also present in the form of strokes of unknown cause.

Fabry patients have progressive kidney impairment, and untreated patients exhibit end-stage renal impairment by the fifth decade of life. Deficiency in α-Gal A activity leads to accumulation of GL-3 and related glycosphingolipids in many cell types including cells in the kidney. GL-3 accumulates in podocytes, epithelial cells and the tubular cells of the distal tubule and loop of Henle. Impairment in kidney function can manifest as proteinuria and reduced glomerular filtration rate.

Because Fabry disease is rare, involves multiple organs, has a wide age range of onset, and is heterogeneous, proper diagnosis is a challenge. Awareness is low among health care professionals and misdiagnoses are frequent. Diagnosis of Fabry disease is most often confirmed on the basis of decreased α-Gal A activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-Gal A enzyme activities ranging from normal to very low activities. Since carriers can have normal α-Gal A enzyme activity in leukocytes, only the identification of an α-Gal A mutation by genetic testing provides precise carrier identification and/or diagnosis.

Mutant forms of α-Gal A are considered to be amenable to migalastat are defined as showing a relative increase (+10 µM migalastat) of ≥1.20-fold and an absolute increase (+10 µM migalastat) of ≥3.0% wild-type (WT) when the mutant form of α-Gal A is expressed in HEK-293 cells (referred to as the "HEK assay") according to Good Laboratory Practice (GLP)-validated in vitro assay (GLP HEK or Migalastat Amenability Assay). Such mutations are also referred to herein as "HEK assay amenable" mutations.

Previous screening methods have been provided that assess enzyme enhancement prior to the initiation of treatment. For example, an assay using HEK-293 cells has been utilized in clinical trials to predict whether a given mutation will be responsive to pharmacological chaperone (e.g., migalastat) treatment. In this assay, cDNA constructs are created. The corresponding α-Gal A mutant forms are transiently expressed in HEK-293 cells. Cells are then incubated ±migalastat (17 nM to 1 mM) for 4 to 5 days. After, α-Gal A levels are measured in cell lysates using a synthetic fluorogenic substrate (4-MU-α-Gal) or by western blot. This has been done for known disease-causing missense or small in-frame insertion/deletion mutations. Mutations that have previously been identified as responsive to a PC (e.g., migalastat) using these methods are listed in U.S. Pat. No. 8,592,362.

Pharmacological Chaperones

The binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the endoplasmic reticulum (Ishii et al., Biochem. Biophys. Res. Comm. 1996; 220: 812-815), the enzyme protein is retarded in the normal transport pathway (endoplasmic reticulum→Golgi apparatus→endosomes→lysosome) and prematurely degraded. Therefore, a compound which binds to and increases the stability of a mutant enzyme, may serve as a "chaperone" for the enzyme and increase the amount that can exit the endoplasmic reticulum and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the endoplasmic reticulum and be trafficked to lysosomes.

In one or more embodiments, the pharmacological chaperone comprises migalastat or salt thereof. As used herein, "migalastat" refers to (2R,3S,4R,5S)-2-(hydroxymethyl) piperdine-3,4,5-triol, and is also known as 1-deoxygalactonojirimycin and known under trade name Galafold™. In further embodiments, the pharmacological chaperone comprises the hydrochloride salt of migalastat. Migalastat has the following structure:

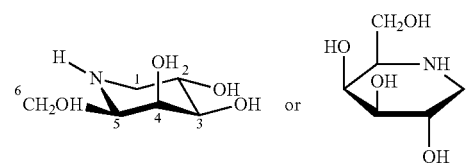

As used herein, the term "free base equivalent" or "FBE" refers to the amount of migalastat present in the migalastat or salt thereof. In other words, the term "FBE" means either an amount of migalastat free base, or the equivalent amount of migalastat free base that is provided by a salt of migalastat. For example, due to the weight of the hydrochloride salt, 150 mg of migalastat hydrochloride only provides as much migalastat as 123 mg of the free base form of migalastat. Other salts will have different conversion factors, depending on the molecular weight of the salt.

Migalastat is a low molecular weight iminosugar and is an analogue of the terminal galactose of GL-3. In vitro and in vivo pharmacologic studies have demonstrated that migalastat acts as a pharmacological chaperone, selectively and reversibly binding, with high affinity, to the active site of wild-type (WT) α-Gal A and specific mutant forms of α-Gal A, the genotypes of which are referred to as HEK assay amenable mutations. Migalastat binding stabilizes these mutant forms of α-Gal A in the endoplasmic reticulum facilitating their proper trafficking to lysosomes where dissociation of migalastat allows α-Gal A to reduce the level of GL-3 and other substrates. Approximately 30-50% of patients with Fabry disease have HEK assay amenable mutations; the majority of which are associated with the classic phenotype of the disease. A list of HEK assay amenable mutations includes at least those mutations listed in Table 1 below. In one or more embodiments, if a double mutation is present on the same chromosome (males and females), that patient is considered HEK assay amenable if the double mutation is present in one entry in Table 1 (e.g., D55V/Q57L). In some embodiments, if a double mutation is present on different chromosomes (only in females) that patient is considered HEK assay amenable if either one of the individual mutations is present in Table 1.

TABLE 1

Amenable Mutations

| Nucleotide change | Nucleotide change | Protein sequence change |
|---|---|---|
| c.7C > G | c.C7G | L3V |
| c.8T > C | c.T8C | L3P |
| c.[11G > T; 620A > C] | c.G11T/A620C | R4M/Y207S |
| c.37G > A | c.G37A | A13T |
| c.37G > C | c.G37C | A13P |
| c.43G > A | c.G43A | A15T |
| c.44C > G | c.C44G | A15G |
| c.53T > G | c.T53G | F18C |
| c.58G > C | c.G58C | A20P |
| c.59C > A | c.C59A | A20D |
| c.70T > C or c.70T > A | c.T70C or c.T70A | W24R |
| c.70T > G | c.T70G | W24G |
| c.72G > C or c.72G > T | c.G72C or c.G72T | W24C |
| c.95T > C | c.T95C | L32P |
| c.97G > T | c.G97T | D33Y |
| c.98A > G | c.A98G | D33G |
| c.100A > G | c.A100G | N34D |
| c.101A > C | c.A101C | N34T |
| c.101A > G | c.A101G | N34S |
| c.102T > G or c.102T > A | c.T102G or c.T102A | N34K |
| c.103G > C or c.103G > A | c.G103C or c.G103A | G35R |
| c.104G > A | c.G104A | G35E |
| c.104G > T | c.G104T | G35V |
| c.107T > C | c.T107C | L36S |
| c.107T > G | c.T107G | L36W |
| c.108G > C or c.108G > T | c.G108C or c.G108T | L36F |
| c.109G > A | c.G109A | A37T |
| c.110C > T | c.C110T | A37V |
| c.122C > T | c.C122T | T41I |
| c.124A > C or c.124A > T | c.A124C or c.A124T | M42L |
| c.124A > G | c.A124G | M42V |
| c.125T > A | c.T125A | M42K |
| c.125T > C | c.T125C | M42T |
| c.125T > G | c.T125G | M42R |
| c.126G > A or c.126G > C or c.126G > T | c.G126A or c.G126C or c.G126T | M42I |
| c.137A > C | c.A137C | H46P |
| c.142G > C | c.G142C | E48Q |
| c.152T > A | c.T152A | M51K |
| c.153G > A or c.153G > T or c.153G > C | c.G153A or c.G153T or c.G153C | M51I |
| c.157A > G | c.A157G | N53D |
| c.[157A > C; 158A > T] | c.A157C/A158T | N53L |
| c.160C > T | c.C160T | L54F |
| c.161T > C | c.T161C | L54P |
| c.164A > G | c.A164G | D55G |
| c.164A > T | c.A164T | D55V |
| c.[164A > T; 170A > T] | c.A164T/A170T | D55V/Q57L |
| c.167G > T | c.G167T | C56F |
| c.167G > A | c.G167A | C56Y |
| c.170A > T | c.A170T | Q57L |
| c.175G > A | c.G175A | E59K |
| c.178C > A | c.C178A | P60T |
| c.178C > T | c.C178T | P60S |
| c.179C > T | c.C179T | P60L |
| c.196G > A | c.G196A | E66K |
| c.197A > G | c.A197G | E66G |
| c.207C > A or c.207C > G | c.C207A or c.C207G | F69L |
| c.214A > G | c.A214G | M72V |
| c.216G > A or c.216G > T or c.216G > C | c.G216A or c.G216T or c.G216C | M72I |
| c.218C > T | c.C218T | A73V |
| c.227T > C | c.T227C | M76T |
| c.239G > A | c.G239A | G80D |
| c.247G > A | c.G247A | D83N |
| c.253G > A | c.G253A | G85S |
| c.254G > A | c.G254A | G85D |
| c.[253G > A; 254G > A] | c.G253A/G254A | G85N |
| c.[253G > A; 254G > T; 255T > G] | c.G253A/G254T/T255G | G85M |
| c.261G > C or c.261G > T | c.G261C or c.G261T | E87D |
| c.265C > T | c.C265T | L89F |
| c.272T > C | c.T272C | I91T |
| c.288G > A or c.288G > T or c.288G > C | c.G288A or c.G288T or c.G288C | M96I |
| c.289G > C | c.G289C | A97P |
| c.290C > T | c.C290T | A97V |

TABLE 1-continued

Amenable Mutations

| Nucleotide change | Nucleotide change | Protein sequence change |
| --- | --- | --- |
| c.305C > T | c.C305T | S102L |
| c.311G > T | c.G311T | G104V |
| c.316C > T | c.C316T | L106F |
| c.322G > A | c.G322A | A108T |
| c.326A > G | c.A326G | D109G |
| c.334C > G | c.C334G | R112G |
| c.335G > A | c.G335A | R112H |
| c.337T > A | c.T337A | F113I |
| c.337T > C or c.339T > A or c.339T > G | c.T337C or c.T339A or c.T339G | F113L |
| c.352C > T | c.C352T | R118C |
| c.361G > A | c.G361A | A121T |
| c.368A > G | c.A368G | Y123C |
| c.373C > T | c.C373T | H125Y |
| c.374A > T | c.A374T | H125L |
| c.376A > G | c.A376G | S126G |
| c.383G > A | c.G383A | G128E |
| c.399T > G | c.T399G | I133M |
| c.404C > T | c.C404T | A135V |
| c.408T > A or c.408T > G | c.T408A or c.T408G | D136E |
| c.416A > G | c.A416G | N139S |
| c.419A > C | c.A419C | K140T |
| c.427G > A | c.G427A | A143T |
| c.431G > A | c.G431A | G144D |
| c.431G > T | c.G431T | G144V |
| c.434T > C | c.T434C | F145S |
| c.436C > T | c.C436T | P146S |
| c.437C > G | c.C437G | P146R |
| c.454T > C | c.T454C | Y152H |
| c.455A > G | c.A455G | Y152C |
| c.466G > A | c.G466A | A156T |
| c.467C > T | c.C467T | A156V |
| c.471G > C or c.471G > T | c.G471C or c.G471T | Q157H |
| c.484T > G | c.T484G | W162G |
| c.493G > C | c.G493C | D165H |
| c.494A > G | c.A494G | D165G |
| c.[496C > G; 497T > G] | c.C496G/T497G | L166G |
| c.496C > G | c.C496G | L166V |
| c.496_497delinsTC | c.496_497delinsTC | L166S |
| c.499C > G | c.C499G | L167V |
| c.506T > C | c.T506C | F169S |
| c.511G > A | c.G511A | G171S |
| c.520T > C | c.T520C | C174R |
| c.520T > G | c.T520G | C174G |
| c.525C > G or c.525C > A | c.C525G or c.C525A | D175E |
| c.539T > G | c.T539G | L180W |
| c.540G > C | c.G540C | L180F |
| c.548G > C | c.G548C | G183A |
| c.548G > A | c.G548A | G183D |
| c.550T > A | c.T550A | Y184N |
| c.551A > G | c.A551G | Y184C |
| c.553A > G | c.A553G | K185E |
| c.559A > G | c.A559G | M187V |
| c.559_564dup | c.559_564dup | p.M187_S188dup |
| c.560T > C | c.T560C | M187T |
| c.561G > T or c.561G > A or c.561G > C | c.G561T or c.G561A or c.G561C | M187I |
| c.572T > A | c.T572A | L191Q |
| c.581C > T | c.C581T | T194I |
| c.584G > T | c.G584T | G195V |
| c.586A > G | c.A586G | R196G |
| c.593T > C | c.T593C | I198T |
| c.595G > A | c.G595A | V199M |
| c.596T > C | c.T596C | V199A |
| c.596T > G | c.T596G | V199G |
| c.599A > G | c.A599G | Y200C |
| c.602C > T | c.C602T | S201F |
| c.602C > A | c.C602A | S201Y |
| c.608A > T | c.A608T | E203V |
| c.609G > C or c.609G > T | c.G609C or c.G609T | E203D |
| c.613C > A | c.C613A | P205T |
| c.613C > T | c.C613T | P205S |
| c.614C > T | c.C614T | P205L |
| c.619T > C | c.T619C | Y207H |
| c.620A > C | c.A620C | Y207S |
| c.623T > G | c.T623G | M208R |

TABLE 1-continued

Amenable Mutations

| Nucleotide change | Nucleotide change | Protein sequence change |
|---|---|---|
| c.628C > T | c.C628T | P210S |
| c.629C > T | c.C629T | P210L |
| c.638A > G | c.A638G | K213R |
| c.638A > T | c.A638T | K213M |
| c.640C > T | c.C640T | P214S |
| c.641C > T | c.C641T | P214L |
| c.643A > G | c.A643G | N215D |
| c.644A > G | c.A644G | N215S |
| c.644A > T | c.A644T | N215I |
| c.[644A > G; 937G > T] | c.A644G/G937T | N215S/D313Y |
| c.646T > G | c.T646G | Y216D |
| c.647A > G | c.A647G | Y216C |
| c.655A > C | c.A655C | I219L |
| c.656T > A | c.T656A | I219N |
| c.656T > C | c.T656C | I219T |
| c.659G > A | c.G659A | R220Q |
| c.659G > C | c.G659C | R220P |
| c.662A > C | c.A662C | Q221P |
| c.671A > C | c.A671C | N224T |
| c.671A > G | c.A671G | N224S |
| c.673C > G | c.C673G | H225D |
| c.683A > G | c.A683G | N228S |
| c.687T > A or c.687T > G | c.T687A or c.T687G | F229L |
| c.695T > C | c.T695C | I232T |
| c.713G > A | c.G713A | S238N |
| c.716T > C | c.T716C | I239T |
| c.720G > C or c.720G > T | c.G720C or c.G720T | K240N |
| c.724A > G | c.A724G | I242V |
| c.724A > T | c.A724T | I242F |
| c.725T > A | c.T725A | I242N |
| c.725T > C | c.T725C | I242T |
| c.728T > G | c.T728G | L243W |
| c.729G > C or c.729G > T | c.G729C or c.G729T | L243F |
| c.730G > A | c.G730A | D244N |
| c.730G > C | c.G730C | D244H |
| c.733T > G | c.T733G | W245G |
| c.740C > G | c.C740G | S247C |
| c.747C > G or c.747C > A | c.C747G or c.C747A | N249K |
| c.749A > C | c.A749C | Q250P |
| c.749A > G | c.A749G | Q250R |
| c.750G > C | c.G750C | Q250H |
| c.758T > C | c.T758C | I253T |
| c.758T > G | c.T758G | I253S |
| c.760-762delGTT | c.760_762delGTT | p.V254del |
| c.769G > C | c.G769C | A257P |
| c.770C > G | c.C770G | A257G |
| c.772G > C or c.772G > A | c.G772C or c.G772A | G258R |
| c.773G > T | c.G773T | G258V |
| c.776C > G | c.C776G | P259R |
| c.776C > T | c.C776T | P259L |
| c.779G > A | c.G779A | G260E |
| c.779G > C | c.G779C | G260A |
| c.781G > A | c.G781A | G261S |
| c.781G > C | c.G781C | G261R |
| c.781G > T | c.G781T | G261C |
| c.788A > G | c.A788G | N263S |
| c.790G > T | c.G790T | D264Y |
| c.794C > T | c.C794T | P265L |
| c.800T > C | c.T800C | M267T |
| c.805G > A | c.G805A | V269M |
| c.806T > C | c.T806C | V269A |
| c.809T > C | c.T809C | I270T |
| c.810T > G | c.T810G | I270M |
| c.811G > A | c.G811A | G271S |
| c.[811G > A; 937G > T] | c.G811A/G937T | G271S/D313Y |
| c.812G > A | c.G812A | G271D |
| c.823C > G | c.C823G | L275V |
| c.827G > A | c.G827A | S276N |
| c.829T > G | c.T829G | W277G |
| c.831G > T or c.831G > C | c.G831T or c.G831C | W277C |
| c.832A > T | c.A832T | N278Y |
| c.835C > G | c.C835G | Q279E |
| c.838C > A | c.C838A | Q280K |
| c.840A > T or c.840A > C | c.A840T or c.A840C | Q280H |
| c.844A > G | c.A844G | T282A |
| c.845C > T | c.C845T | T282I |

TABLE 1-continued

Amenable Mutations

| Nucleotide change | Nucleotide change | Protein sequence change |
|---|---|---|
| c.850A > G | c.A850G | M284V |
| c.851T > C | c.T851C | M284T |
| c.860G > T | c.G860T | W287L |
| c.862G > C | c.G862C | A288P |
| c.866T > G | c.T866G | I289S |
| c.868A > C or c.868A > T | c.A868C or c.A868T | M290L |
| c.869T > C | c.T869C | M290T |
| c.870G > A or c.870G > C or c.870G > T | c.G870A or c.G870C or c.G870T | M290I |
| c.871G > A | c.G871A | A291T |
| c.877C > A | c.C877A | P293T |
| c.881T > C | c.T881C | L294S |
| c.884T > G | c.T884G | F295C |
| c.886A > G | c.A886G | M296V |
| c.886A > T or c.886A > C | c.A886T or c.A886C | M296L |
| c.887T > C | c.T887C | M296T |
| c.888G > A or c.888G > T or c.888G > C | c.G888A or c.G888T or c.G888C | M296I |
| c.893A > G | c.A893G | N298S |
| c.897C > G or c.897C > A | c.C897G or c.C897A | D299E |
| c.898C > T | c.C898T | L300F |
| c.899T > C | c.T899C | L300P |
| c.901C > G | c.C901G | R301G |
| c.902G > C | c.G902C | R301P |
| c.902G > A | c.G902A | R301Q |
| c.902G > T | c.G902T | R301L |
| c.907A > T | c.A907T | I303F |
| c.908T > A | c.T908A | I303N |
| c.911G > A | c.G911A | S304N |
| c.911G > C | c.G911C | S304T |
| c.919G > A | c.G919A | A307T |
| c.922A > G | c.A922G | K308E |
| c.924A > T or c.924A > C | c.A924T or c.A924C | K308N |
| c.925G > C | c.G925C | A309P |
| c.926C > T | c.C926T | A309V |
| c.928C > T | c.C928T | L310F |
| c.931C > G | c.C931G | L311V |
| c.935A > G | c.A935G | Q312R |
| c.936G > T or c.936G > C | c.G936T or c.G936C | Q312H |
| c.937G > T | c.G937T | D313Y |
| c.[937G > T; 1232G > A] | c.G937T/G1232A | D313Y/G411D |
| c.938A > G | c.A938G | D313G |
| c.946G > A | c.G946A | V316I |
| c.947T > G | c.T947G | V316G |
| c.950T > C | c.T950C | I317T |
| c.955A > T | c.A955T | I319F |
| c.956T > C | c.T956C | I319T |
| c.959A > T | c.A959T | N320I |
| c.962A > G | c.A962G | Q321R |
| c.962A > T | c.A962T | Q321L |
| c.963G > C or c.963G > T | c.G963C or c.G963T | Q321H |
| c.964G > A | c.G964A | D322N |
| c.964G > C | c.G964C | D322H |
| c.966C > A or c.966C > G | c.C966A or c.C966G | D322E |
| c.968C > G | c.C968G | P323R |
| c.973G > A | c.G973A | G325S |
| c.973G > C | c.G973C | G325R |
| c.978G > C or c.978G > T | c.G978C or c.G978T | K326N |
| c.979C > G | c.C979G | Q327E |
| c.980A > T | c.A980T | Q327L |
| c.983G > C | c.G983C | G328A |
| c.989A > G | c.A989G | Q330R |
| c.1001G > A | c.G1001A | G334E |
| c.1010T > C | c.T1010C | F337S |
| c.1012G > A | c.G1012A | E338K |
| c.1016T > A | c.T1016A | V339E |
| c.1027C > A | c.C1027A | P343T |
| c.1028C > T | c.C1028T | P343L |
| c.1033T > C | c.T1033C | S345P |
| c.1046G > C | c.G1046C | W349S |
| c.1055C > G | c.C1055G | A352G |
| c.1055C > T | c.C1055T | A352V |
| c.1061T > A | c.T1061A | I354K |
| c.1066C > G | c.C1066G | R356G |
| c.1066C > T | c.C1066T | R356W |
| c.1067G > A | c.G1067A | R356Q |

TABLE 1-continued

Amenable Mutations

| Nucleotide change | Nucleotide change | Protein sequence change |
|---|---|---|
| c.1067G > C | c.G1067C | R356P |
| c.1072G > C | c.G1072C | E358Q |
| c.1073A > C | c.A1073C | E358A |
| c.1073A > G | c.A1073G | E358G |
| c.1074G > T or c.1074G > C | c.G1074T or c.G1074C | E358D |
| c.1076T > C | c.T1076C | I359T |
| c.1078G > A | c.G1078A | G360S |
| c.1078G > T | c.G1078T | G360C |
| c.1079G > A | c.G1079A | G360D |
| c.1082G > A | c.G1082A | G361E |
| c.1082G > C | c.G1082C | G361A |
| c.1084C > A | c.C1084A | P362T |
| c.1085C > T | c.C1085T | P362L |
| c.1087C > T | c.C1087T | R363C |
| c.1088G > A | c.G1088A | R363H |
| c.1102G > A | c.G1102A | A368T |
| c.1117G > A | c.G1117A | G373S |
| c.1124G > A | c.G1124A | G375E |
| c.1153A > G | c.A1153G | T385A |
| c.1168G > A | c.G1168A | V390M |
| c.1172A > C | c.A1172C | K391T |
| c.1184G > A | c.G1184A | G395E |
| c.1184G > C | c.G1184C | G395A |
| c.1192G > A | c.G1192A | E398K |
| c.1202_1203insGACTTC | c.1202_1203insGACTTC | p.T400_S401dup |
| c.1208T > C | c.T1208C | L403S |
| c.1225C > G | c.C1225G | P409A |
| c.1225C > T | c.C1225T | P409S |
| c.1225C > A | c.C1225A | P409T |
| c.1228A > G | c.A1228G | T410A |
| c.1229C > T | c.C1229T | T410I |
| c.1232G > A | c.G1232A | G411D |
| c.1235C > A | c.C1235A | T412N |
| c.1253A > G | c.A1253G | E418G |
| c.1261A > G | c.A1261G | M421V |

Dosing, Formulation and Administration

In one or more embodiments, the Fabry patient is administered migalastat or salt thereof at a frequency of once every other day (also referred to as "QOD"). In various embodiments, the doses described herein pertain to migalastat hydrochloride or an equivalent dose of migalastat or a salt thereof other than the hydrochloride salt. In some embodiments, these doses pertain to the free base of migalastat. In alternate embodiments, these doses pertain to a salt of migalastat. In further embodiments, the salt of migalastat is migalastat hydrochloride. The administration of migalastat or a salt of migalastat is referred to herein as "migalastat therapy".

It is noted that 150 mg of migalastat hydrochloride is equivalent to 123 mg of the free base form of migalastat. Thus, in one or more embodiments, the dose is 150 mg of migalastat hydrochloride or an equivalent dose of migalastat or a salt thereof other than the hydrochloride salt, administered at a frequency of once every other day. As set forth above, this dose is referred to as 123 mg FBE of migalastat. In further embodiments, the dose is 150 mg of migalastat hydrochloride administered every other day. In other embodiments, the dose is 123 mg of the migalastat free base administered at a frequency of once every other day.

Accordingly, in various embodiments, migalastat therapy includes administering 123 mg FBE every other day, such as 150 mg of migalastat hydrochloride every other day.

The administration of migalastat may be for a certain period of time. In one or more embodiments, the migalastat is administered for at least 28 days, such as at least 30, 60 or 90 days or at least 3, 4, 5, 6, 7, 8, 9, 10, 11, 12, 16, 20, 24, 30 or 36 months or at least 1, 2, 3, 4 or 5 years. In various embodiments, the migalastat therapy is long-term migalastat therapy of at least 6 months, such as at least 6, 7, 8, 9, 10, 11, 12, 16, 20, 24, 30 or 36 months or at least 1, 2, 3, 4 or 5 years.

Administration of migalastat according to the present invention may be in a formulation suitable for any route of administration, but is preferably administered in an oral dosage form such as a tablet, capsule or solution. As one example, the patient is orally administered capsules each containing 150 mg migalastat hydrochloride or an equivalent dose of migalastat or a salt thereof other than the hydrochloride salt.

In some embodiments, the PC (e.g., migalastat or salt thereof) is administered orally. In one or more embodiments, the PC (e.g., migalastat or salt thereof) is administered by injection. The PC may be accompanied by a pharmaceutically acceptable carrier, which may depend on the method of administration.

In one embodiment of the invention, the PC (e.g., migalastat or salt thereof) is administered as monotherapy, and can be in a form suitable for any route of administration, including e.g., orally in the form tablets or capsules or liquid, in sterile aqueous solution for injection, or in a dry lyophilized powder to be added to the formulation of the replacement enzyme during or immediately after reconstitution to prevent enzyme aggregation in vitro prior to administration.

When the PC (e.g., migalastat or salt thereof) is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active chaperone compound.

The pharmaceutical formulations of the PC (e.g., migalastat or salt thereof) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the purified enzyme (if any) and the PC (e.g., migalastat or salt thereof) in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The route of administration of the chaperone compound may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the chaperone compound may be by periodic injections of a bolus of the preparation, or may be administered by intravenous or intraperitoneal administration from a reservoir which is external (e.g., an i.v. bag) or internal (e.g., a bioerodable implant).

Embodiments relating to pharmaceutical formulations and administration may be combined with any of the other embodiments of the invention, for example embodiments relating to methods of treating patients with Fabry disease, methods of treating ERT-naïve Fabry patients, methods of treating ERT-experienced Fabry patients, methods of reducing LVM, methods of reducing LVMi, methods of normalizing LVMi, methods of reducing podocyte GL-3, methods of reducing podocyte volume, methods of reducing GL-3 inclusion volume in podocytes, methods of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, the PCs and suitable dosages thereof.

In one or more embodiments, the PC (e.g., migalastat or salt thereof) is administered in combination with ERT. ERT increases the amount of protein by exogenously introducing wild-type or biologically functional enzyme by way of infusion. This therapy has been developed for many genetic disorders, including lysosomal storage disorders such as Fabry disease, as referenced above. After the infusion, the exogenous enzyme is expected to be taken up by tissues through non-specific or receptor-specific mechanism. In general, the uptake efficiency is not high, and the circulation time of the exogenous protein is short. In addition, the exogenous protein is unstable and subject to rapid intracellular degradation as well as having the potential for adverse immunological reactions with subsequent treatments. In one or more embodiments, the chaperone is administered at the same time as replacement enzyme (e.g., replacement α-Gal A). In some embodiments, the chaperone is co-formulated with the replacement enzyme (e.g., replacement α-Gal A).

In one or more embodiments, a patient is switched from ERT to migalastat therapy. In some embodiments, a patient on ERT is identified, the patient's ERT is discontinued, and the patient begins receiving migalastat therapy. The migalastat therapy can be in accordance with any of the methods described herein.

Left Ventricular Mass

The dosing regimens described herein can improve LVM or LVMi in Fabry patients. The natural history of LVMi and cardiac hypertrophy in untreated Fabry patients regardless of phenotype (Patel, O'Mahony et al. 2015) is a progressive increase in LVMi between +4.07 and +8.0 g/m²/year (Kampmann, Linhart et al. 2008; Wyatt, Henley et al. 2012; Germain, Weidemann et al. 2013). As untreated Fabry patients typically exhibit an increase in LVMi over time, both decreases in and maintenance of LVMi are indications of a benefit of migalastat therapy. As described in further detail in the Examples below, Phase 3 studies have found that migalastat therapy decreases LVMi in both ERT-experienced and ERT-naïve patients, with even greater reductions in LVMi shown in patients with LVH at baseline. These Phase 3 studies also found that migalastat therapy normalizes LVMi in some patients with LVH. Accordingly, migalastat therapy can be used to treat Fabry patients by reducing LVM, reducing LVMi and/or normalizing LVMi in ERT-naïve and/or ERT-experienced Fabry patients, including patients with LVH.

The Phase 3 studies of migalastat therapy evaluated LVMi, which is considered a more accurate measure than LVM. Also, in the Phase 3 studies, the echocardiograms were conducted locally, but the echocardiograms were all centrally read by the same reader. Using the same reader to centrally read the echocardiograms improves accuracy compared to reading the echocardiograms locally.

The migalastat therapy may reduce the increase in LVMi for a Fabry patient compared to the same patient without treatment with migalastat therapy. In one or more embodiments, the migalastat therapy provides a change in LVMi for a patient that is less than (i.e., more negative than) 0 g/m², such as less than or equal to about $-0.5, -1, -1.5, -2, -2.5, -3, -3.5, -4, -4.5, -5, -5.5, -6, -7, -8, -9, -10, -11, -12, -13, -14, -15, -16, -17, -18, -19$ or $-20$ g/m². Expressed differently, in one or more embodiments, the migalastat therapy provides a reduction in LVMi of greater than 0 g/m², such as reductions of at least about 0.5, 1, 1.5, 2, 2.5, 3, 3.5, 4, 4.5, 5, 5.5, 6, 7, 8, 9, 10, 11, 12, 13, 14, 15, 16, 17, 18, 19 or 20 g/m².

In one or more embodiments, the migalastat therapy provides an average decrease of LVMi in a group of ERT-experienced patients of at least about 1 g/m² after 18 months of administration of migalastat or a salt thereof. In various embodiments, the average decrease in the group of ERT-experienced patients after 18 months of administration of migalastat or a salt thereof is at least about 1, 2, 3, 4, 5 or 6 g/m², such as about 6.6 g/m².

In one or more embodiments, the migalastat therapy provides an average decrease of LVMi in a group of ERT-experienced patients of at least about 1 g/m² after 18 months of administration of migalastat or a salt thereof. In various embodiments, the average decrease in the group of ERT-experienced patients after 18 months of administration of migalastat or a salt thereof is at least about 1, 2, 3, 4, 5, 6, 7 or 8 g/m², such as about 8.4 g/m².

In one or more embodiments, the migalastat therapy provides an average decrease of LVMi in a group of ERT-experienced patients of at least about 0.5 g/m² after 30 months of administration of migalastat or a salt thereof. In various embodiments, the average decrease in the group of ERT-experienced patients after 30 months of administration of migalastat or a salt thereof is at least about 0.5, 1, 1.5, 2, 2.5, 3, 3.5 or 4 g/m², such as about 3.8 g/m².

In one or more embodiments, the migalastat therapy provides an average decrease of LVMi in a group of ERT-experienced patients with LVH of at least about 1 g/m² after 30 months of administration of migalastat or a salt thereof. In various embodiments, the average decrease in the group of ERT-experienced patients with LVH after 30 months of administration of migalastat or a salt thereof is at least about 1, 2, 3, 4, 5, 6, 8, 8 or 9 g/m², such as about 9 g/m².

In one or more embodiments, the migalastat therapy provides an average decrease of LVMi in a group of ERT-naïve patients of at least about 1 g/m² after 18 to 24 months of administration of migalastat or a salt thereof. In various embodiments, the average decrease in the group of ERT-naïve patients after 18 to 24 months of administration of migalastat or a salt thereof is at least about 1, 2, 3, 4, 5, 6 or 7 g/m², such as about 7.7 g/m².

In one or more embodiments, the migalastat therapy provides an average decrease of LVMi in a group of ERT-naïve patients with LVH of at least about 1 g/m² after 18 to 24 months of administration of migalastat or a salt thereof. In various embodiments, the average decrease in the group of ERT-naïve with LVH patients after 18 to 24 months of administration of migalastat or a salt thereof is at least about 1, 2, 3, 4, 5, 6, 7, 8, 9, 10, 11, 12, 13, 14, 15, 16, 17 or 18 g/m², such as about 18.6 g/m².

In one or more embodiments, the migalastat therapy provides an average decrease of LVMi in a group of ERT-naïve patients of at least about 1 g/m² after 30 to 36 months of administration of migalastat or a salt thereof. In various embodiments, the average decrease in the group of ERT-naïve patients after 30 to 36 months of administration of migalastat or a salt thereof is at least about 1, 2, 3, 4, 5, 6, 7, 8, 9, 10, 11, 12, 13, 14, 15, 16 or 17 g/m², such as about 17 g/m².

In one or more embodiments, the migalastat therapy provides an average decrease of LVMi in a group of ERT-naïve patients with LVH of at least about 1 g/m² after 30 to 36 months of administration of migalastat or a salt thereof. In various embodiments, the average decrease in the group of ERT-naïve patients with LVH after 30 to 36 months of administration of migalastat or a salt thereof is at least about 1, 2, 3, 4, 5, 6, 7, 8, 9, 10, 11, 12, 13, 14, 15, 16, 17, 18, 19 or 20 g/m², such as about 20.8 g/m².

Podocyte GL-3 and Podocyte Volume

The dosing regimens described herein can improve one or more parameters related to podocytes in Fabry patients. Fabry patients typically accumulate GL-3 in podocyte cells. As described in further detail in the Examples below, a Phase 3 study has found that migalastat therapy reduces mean podocyte volume and reduces mean podocyte GL-3 inclusion volume. Accordingly, migalastat therapy can be used to treat Fabry patients by reducing podocyte GL-3, reducing podocyte volume and/or reducing GL-3 inclusion volume in podocytes.

The Phase 3 study of migalastat therapy evaluated podocyte GL-3 according to two methodologies. In the first methodology, a qualitative comparison of GL-3 for podocytes was performed, as a reliable quantitative approach was not available at the time of this study. The pathologists assessed side-by-side digital images of baseline and post-baseline biopsies (blinded to treatment assignment and visit date), and categorized the biopsies as having more, less or equal GL-3 in the podocytes. Of note, if a score of either more or less GL-3 was assigned, then this indicates that there was a visually apparent change in GL-3 between baseline and post-baseline. Three pathologists determined in a blinded fashion whether paired biopsies had an "equal" number of GL-3 inclusions within each cell type, or whether one in the pair had "less" or "more" inclusions. If 2 pathologists agreed on "less" or "more" that agreed value was assigned, otherwise a designation of "equal" was retained. Results were summarized as percent of specimens with increases, decreases, or no change in GL-3 inclusions relative to baseline.

In the second methodology, a post-hoc analysis was performed using stereological principles to estimate structural parameters including average podocyte volume, fractional volume of GL-3 inclusions within podocytes, and total volume of GL-3 inclusions per podocyte. These stereological principles, which are based on stochastic geometry and statistics, are designed to be unbiased, efficient, and reproducible. Electron microscopic images (~30,000×), taken according to a systematic, unbiased, uniform random sampling method from glomeruli were used to estimate fractional volume (Vv) of GL-3 inclusions in podocytes [Vv(Inc/PC)]. Grids with appropriate point densities were superimposed over the images. The parameters were calculated by dividing the number of grid points hitting GL-3 inclusions by the number of grid points hitting cytoplasm of glomerular podocytes.

In one or more embodiments, the migalastat therapy may reduce the podocyte volume for a Fabry patient compared to the same patient without treatment with migalastat therapy. In one or more embodiments, the migalastat therapy reduces the podocyte volume by at least about 10%, such as at least about 15, 20, 25, 30, 35, 40, 45 or 50%.

In one or more embodiments, the migalastat therapy provides an average reduction of podocyte volume in a group of ERT-naïve patients of at least about 10% after 6 months of administration of migalastat or a salt thereof. In various embodiments, the average reduction in the group of ERT-naïve patients after 6 months of administration of migalastat or a salt thereof is at least about 10, 15, 20, 25, 30, 35, 40, 45 or 50%, such as about 47%.

In one or more embodiments, the migalastat therapy may reduce the total GL-3 inclusion volume per podocyte for a Fabry patient compared to the same patient without treatment with migalastat therapy. In one or more embodiments, the migalastat therapy reduces the podocyte GL-3 inclusion volume by at least about 10%, such as at least about 15, 20, 25, 30, 35, 40, 45 or 50%.

In one or more embodiments, the migalastat therapy provides an average reduction of total GL-3 inclusion volume per podocyte in a group of ERT-naïve patients of at least about 10% after 6 months of administration of migalastat or a salt thereof. In various embodiments, the average reduction in the group of ERT-naïve patients after 6 months of administration of migalastat or a salt thereof is at least about 10, 15, 20, 25, 30, 35, 40, 45 or 50%, such as about 50%.

EXAMPLES

Example 1: Dosing Regimens for the Treatment of ERT-Naïve Fabry Patients Using Migalastat Hydrochloride This example describes a Phase 3 study of migalastat therapy in ERT-naïve Fabry patients.

Patient Enrollment.

Eligible patients were 16-74 years old and had genetically-confirmed Fabry disease; had either never received or had not received ERT for ≥6 months; had a GLA mutation that resulted in a mutant protein that would respond to migalastat, based on the human embryonic kidney-293 (HEK) assay used at the time of enrollment; had an eGFR >30 ml/minute/1.73 m$^2$, and had a urinary GL-3≥4 times the upper limit of normal.

Study Design.

Following eligibility-baseline assessments (2 months), patients were randomized to Stage 1—6 months of double-blind administration of 150 mg migalastat hydrochloride or placebo every other day. All patients completing Stage 1 were eligible to receive open-label migalastat in Stage 2 (months 6-12) and for an additional year (months 13-24) thereafter. The primary objective was to compare the effect of migalastat to placebo on kidney GL-3 as assessed by histological scoring of the number of inclusions in interstitial capillaries after 6 months of treatment. The secondary objectives of Stage 1 were to compare the effect of migalastat to placebo on urine GL-3 levels, on renal function, 24-hours urinary protein, and on safety and tolerability. The tertiary objectives were cardiac function, patient-reported outcomes, exploratory kidney analyses, and white blood cell α-Gal A activity. Study completers were eligible to enroll in the open-label extension study for up to 5 years.

Kidney Histology Assessment.

Each patient underwent a baseline kidney biopsy, as well as repeat kidney biopsies at 6 and 12 months. The number of GL-3 inclusions per kidney interstitial capillary per patient at baseline, and at 6 and 12 months was quantitatively assessed in 300 capillaries by 3 independent pathologists blinded to treatment and visit. All values for each individual biopsy at a given time were averaged prior to statistical analysis.

GL-3 changes in podocytes, endothelial cells, and mesangial cells, and glomerular sclerosis, were assessed qualitatively by the same 3 pathologists blinded to treatment/visit.

Globotriaosylceramide and Globotriaosylsphingosine.

Plasma lyso-Gb3 and 24-hour urine GL-3 were analyzed by liquid chromatography-mass-spectroscopy using a novel stable isotope-labeled internal standard, 13C6-lyso-Gb3 (lower-limit-of-quantification: 0.200 ng/mL, 0.254 nmol/L).

Renal Function Assessment.

Annualized rates of change (mL/min/1.73 m$^2$/year) were calculated using Chronic Kidney Disease Epidemiology Collaboration-eGFR$_{CKD\text{-}EPI}$) and measured iohexol clearance-mGFR$_{iohexol}$).

Echocardiography.

LVMi, left posterior wall thickness, diastolic, interventricular septum thickness, diastolic and other parameters were assessed through blinded, centralized evaluation.

Patient-Reported Outcomes.

Patient-reported outcomes were assessed using the Gastrointestinal-Symptoms-Rating-Scale (GSRS), Short Form-36v2™ and Brief-Pain-Inventory-Pain-Severity-Component.

Safety Analysis and Adverse Events.

Randomized patients receiving ≥1 dose were included in the safety analysis, which comprised vital signs, physical exams, electrocardiograms, clinical labs, and adverse events.

Statistical Analyses for Kidney Interstitial Capillary GL-3 Substrate.

The primary Stage 1 (6 month) endpoint (ITT population with baseline biopsies, n=64) was the proportion of patients in the migalastat and placebo groups with a ≥50% reduction in GL-3 inclusions per interstitial capillary. Two other Stage 1 endpoints were assessed (modified-ITT population: randomized patients with paired baseline and month 6 biopsies; n=60): percent change in GL-3 inclusions per interstitial capillary, and percent of interstitial capillaries with zero GL-3 inclusions.

Efficacy analyses for GL-3 inclusions per interstitial capillary and other prespecified endpoints in Stage 2 (months 6-12) and the open-label-extension (months 12-24) were based on the modified intention to treat (mITT)—population consisting of randomized patients with mutant α-Gal A enzyme shown to be suitable for migalastat treatment by the validated assay; n=50).

Results

Baseline Characteristics.

Sixty-seven patients (16-74 years-old; 64% female) with potentially responsive mutant α-Gal A were randomized (ITT population). Table 2 provides the baseline characteristics for the 50 patients in the ITT population with suitable mutant α-Gal A. There were no statistically significant differences in baseline parameters.

TABLE 2

Baseline Characteristics

| Parameter | Treatment Group | | |
|---|---|---|---|
| | Migalastat HCl (N = 28) | Placebo to Migalastat HCl (N = 22) | Total (N = 50) |
| Age (year) (n) | 28 | 22 | 50 |
| Mean ± SD | 41.5 ± 13 | 45.1 ± 8.0 | 43.1 ± 11 |
| Median | 37.0 | 45.5 | 45.0 |
| Weight (kg) (n) | 28 | 22 | 50 |
| Mean ± SD | 72.6 ± 15.35 | 76.1 ± 16.52 | 74.1 ± 15.81 |
| Median | 72.3 | 74.0 | 72.8 |
| Number of Years of Diagnosis of Fabry Disease (n) | 28 | 21 | 49 |
| Mean ± SD | 5.6 ± 6.89 | 7.3 ± 8.80 | 6.3 ± 7.73 |
| Median | 4.1 | 4.1 | 4.1 |
| Number of patients previously on ERT (>6 months prior to baseline) (%) | 4 (14.3%) | 7 (31.8%) | 11 (22.0%) |
| Use of ACEi/ARB/Ri at Baseline | | | |
| Yes (%) | 9 (32.1%) | 12 (54.5%) | 21 (42.0%) |
| No (%) | 19 (67.9%) | 10 (45.5%) | 29 (58.0%) |
| Proteinuria > 150 mg/24 h (%) | 17 (60.7%) | 18 (81.8%) | 35 (70.0%) |
| Proteinuria > 300 mg/24 h (%) | 8 (28.6%) | 11 (50.0%) | 19 (38.0%) |
| Proteinuria > 1000 mg/24 h (%) | 3 (10.7%) | 3 (13.6%) | 6 (12.0%) |
| mGFR$_{Iohexol}$ (mL/min/1.73 m$^2$) (n) | 27 | 21 | 48 |
| Mean ± SD | 79.95 ± 30.9 | 83.12 ± 22.8 | 81.34 ± 27.5 |
| Median | 84.90 | 82.20 | 83.40 |
| eGFR$_{CKD-EPI}$ (mL/min/1.73 m$^2$) | 28 | 22 | 50 |
| Mean ± SD | 94.4 ± 27.0 | 90.6 ± 17.1 | 92.7 ± 23.0 |
| Median | 96.6 | 93.5 | 94.0 |
| Lyso-Gb$_3$ (n) | 18 | 13 | 31 |
| Mean (nmol/L) ± SD | 47.3 ± 62 | 41.9 ± 39 | 45.0 ± 53 |

Published reports of clinical phenotype(s) associated with the genotypes of patients with suitable mutations (n=50) indicate that 30 (60%) had mutations associated with the classic phenotype of Fabry disease, one (2%) with the non-classic phenotype, three (6%) with both phenotypes, and 16 (32%) not yet classified. Residual WBC α-Gal A activity <3% was found in 14 of 16 (87%) males; 29 of 31 (94%) males and females had elevated plasma lyso-Gb3, and 47 of 50 (94%) males and females had multi-organ system disease.

Migalastat and Kidney Interstitial Capillary GL-3.

In the 6-month primary outcome analysis (ITT), 13 of 32 (41%) migalastat and 9 of 32 (28%) placebo-treated patients achieved a response (≥50% reduction in GL-3 inclusions per interstitial capillary) (p=0.30). The median change in interstitial capillary GL-3 from baseline was −40.8% for migalastat versus −5.59% for placebo (p=0.097). The mean difference for the change in % of interstitial capillaries with zero GL-3 inclusions was 7.3% in favor of migalastat (p=0.042).

In Stage 1 (6-month post hoc) and Stage 2 (12-month prespecified) analyses (mITT-suitable population; n=45), 6 months of migalastat was associated with a significantly greater reduction in interstitial capillary GL-3 (±SEM) compared to placebo: −0.250±0.103 versus +0.071±0.126; p=0.008. The reduction in interstitial capillary GL-3 at 6 months remained stable following an additional 6 months of treatment. A significant reduction in interstitial capillary GL-3 (±SEM) was observed at 12 months in patients switching from placebo to migalastat at 6 months (−0.330±0.152; p=0.014). Patients with mutant α-Gal A that was not suitable for migalastat therapy according to the validated assay did not show any treatment effect in interstitial capillary GL-3.

Migalastat and GL-3 in Glomerular Cells.

Based on qualitative assessments on 23 kidney biopsies, following 12 months of migalastat, patients with responsive mutant α-Gal A showed decreases in glomerular podocyte (5 of 23 biopsies; 22%), endothelial cell (6 of 23 biopsies; 26%), and mesangial cell GL-3 (11 of 23 biopsies; 48%). None of the samples had increases; the remaining samples showed no change.

Migalastat and Plasma Lyso-Gb3 Levels.

Six months of migalastat (mITT-suitable) was associated with a significant reduction in plasma lyso-Gb3 levels compared to placebo (p=0.0033). Plasma lyso-Gb3 remained stable without further reduction following 6 additional months of migalastat. A significant reduction in plasma lyso-Gb3 was found in patients (ITT-suitable) switching from placebo to migalastat between 6 and 12 months (p<0.0001). Plasma levels in patients with mutant α-Gal A that was not suitable were unchanged.

Migalastat and Urine GL-3 Substrate.

In patients with suitable mutant α-Gal A, mean changes in 24-hour urine GL-3 substrate (±SEM) concentration for migalastat and placebo (baseline to month 6) were: −361±169 (to 555±151) and −147±217 (to 1017±218) ng/mg creatinine, respectively (p=0.44).

Migalastat and Kidney Function.

There were no statistically significant differences between the migalastat and placebo arms in $eGFR_{CKD-EPI}$, or $mGFR_{iohexol}$ changes from baseline to month 6 (mITT-suitable).

In patients followed for up to 24 months of migalastat (mITT-suitable), the annualized changes in $eGFR_{CKD-EPI}$, and $mGFR_{iohexol}$ (±SEM) were −0.30±6.6, and −1.51±1.33 mL/min/1.73 m$^2$, respectively. Male gender and higher baseline proteinuria were associated with higher rate of annual decline. There were no statistically significant differences in baseline levels or changes from baseline between treatment groups for 24-hour urine protein.

Migalastat and Echocardiographic Parameters.

At baseline, left-ventricular-mass-index was comparable between groups with no significant differences in Stage 1.

In patients (ITT-suitable), who received migalastat for up to 24 months, a statistically significant decrease in left-ventricular-mass-index (LVMi) (p<0.05 based on the 95% CI not including 0) was observed overall with a trend toward a larger reduction in patients with baseline LV hypertrophy. Table 3 shows the echocardiographic-derived LVMi changes from baseline to month 18/24 for ITT-suitable patients.

TABLE 3

| LVMi Changes (ITT-Suitable) | | |
| --- | --- | --- |
| Patients with Suitable Mutant α-Gal A[1] | Baseline[2] Mean ± SEM (g/m$^2$) | Change from Baseline to Month 18/24[3] Mean ± SEM (95% CI) |
| All | 96.5 ± 5.0 n = 44 | −7.69 ± 3.7 (−15.4, −0.009)[4] n = 27 |
| Patients with LVH at baseline | 138.9 ± 11 n = 11 | −18.6 ± 8.3 (−38.2, 1.04) n = 8 |

LVMi, Left-ventricular-mass-index (g/m$^2$): Normal: 43-95 (female), 49-115 (male);
[1]Includes patients with a baseline and post-baseline ECHO, who received ≥18-months migalastat.
[2]Month 6 used as baseline for placebo patients switching to migalastat; Baseline used if no month 6.
[3]Baseline of extension study used as month 18/24.
[4]Statistically significantly different from baseline based on 95% CIs not overlapping with 0; p < 0.05

Interventricular septal wall thickness decreased by 0.061 cm±0.051 (5.2%) from baseline (1.17 cm±0.057) (95% CI: −1.67, 0.045); the left ventricular posterior wall thickness was stable for up to 24 months. The changes in left-ventricular-mass-index correlated with changes in IVSWT ($R^2$=0.26, p=0.006) but not with changes in left ventricular posterior wall thickness ($R^2$=0.06, p=0.230).

LVMi continued to decrease over 30/36 months of migalastat treatment in an extension of this study, with mean change from baseline of −17.0 g/m$^2$ ([95% CI −26.2, −7.9]; n=15)]. In patients with baseline LVH (n=11), the change from baseline was larger and statistically, −20.8 g/m$^2$ [−95% CI −57.9, −2.2]. The LVMi changes from baseline to after 6/12, 18/24 and 30/36 months of migalastat therapy are shown in FIG. 3. In the extension of the study to 30/36 months, 82% (9/11) and 46% (5/11) of the patients with LVH at baseline had reductions and normalizations of LVMi, respectively.

Gastrointestinal Symptoms Rating Scale.

Gastrointestinal symptoms improved in 3 of 5 domains (diarrhea, reflux, indigestion) in migalastat-treated ITT-suitable patients, as shown in Table 4 below.

For the diarrhea domain, between baseline and month 6 (Stage 1), there was a statistically significant decrease (p=0.03; ITT-suitable); a nonsignificant decrease was also observed for ITT-suitable patients with baseline symptoms (p=0.06). Statistically significant changes over 24 months were found for ITT-suitable patients and ITT-suitable patients with baseline symptoms (p<0.05, based on the 95% CI not including 0).

There was a statistically significant improvement in the reflux domain in Stage 1 in ITT-suitable patients with baseline symptoms (p=0.047). Statistically significant changes over 24 months were found in the indigestion domain for ITT-suitable patients and ITT-suitable patients with baseline symptoms (p<0.05 based on the 95% CI not including 0). There was a trend toward improvement in the constipation domain.

TABLE 4

| | Changes in Gastrointestinal Symptoms Rating Scale[1] (ITT-Suitable) | | | | | | | | | |
| --- | --- | --- | --- | --- | --- | --- | --- | --- | --- | --- |
| | GSRS Domain | | | | | | | | | |
| Treatment | Diarrhea | | Reflux | | Indigestion | | Constipation | | Abdominal Pain | |
| Group | Migalastat | Placebo | Migalastat | Placebo | Migalastat | Placebo | Migalastat | Placebo | Migalastat | Placebo |
| Mean Baseline Values (n) | | | | | | | | | | |
| All patients | 2.3 (28) | 2.1 (22) | 1.4 (28) | 1.4 (22) | 2.5 (28) | 2.4 (22) | 1.9 (28) | 2.0 (22) | 2.1 (28) | 2.3 (22) |
| Patients with Symptoms at BL | 3.2 (17) | 3.1 (11) | 2.1 (10) | 2.6 (6) | 2.8 (23) | 2.7 (19) | 2.5 (17) | 2.4 (15) | 2.4 (22) | 2.9 (15) |

TABLE 4-continued

Changes in Gastrointestinal Symptoms Rating Scale[1] (ITT-Suitable)

| Treatment Group | Diarrhea | | Reflux | | Indigestion | | Constipation | | Abdominal Pain | |
|---|---|---|---|---|---|---|---|---|---|---|
| | Migalastat | Placebo | Migalastat | Placebo | Migalastat | Placebo | Migalastat | Placebo | Migalastat | Placebo |
| Change from Baseline to Month 6 (Stage 1, Double-Blind) | | | | | | | | | | |
| All Patients | −0.3*[2] | +0.2 | −0.1 | +0.2 | −0.1 | −0.1 | +0.1 | +0.2 | 0.0 | 0.0 |
| Patients with Symptoms at BL | −0.6 | +0.2 | −0.6*[3] | +0.6 | −0.2 | −0.2 | +0.2 | +0.1 | −0.1 | −0.1 |
| Change from Baseline (Migalastat) or Month 6 (Placebo) to Month 24 (OLE Migalastat Treatment) | | | | | | | | | | |
| All Patients | −0.5 (−0.9, −0.1)*[4] | | −0.2 (−0.5, 0.2) | | −0.4 (−0.7, −0.04)*[4] | | −0.4 (−0.7, +0.0)*[5] | | −0.2 (−0.5, +0.1) | |
| Patients with Symptoms at BL | −1.0 (−1.5, −0.4)*[4] | | −0.6 (−1.5, 0.2) | | −0.5 (−0.8, −0.06)*[4] | | −0.5 (−1.1, +0.0)*[5] | | −0.2 (−0.6, 0.1) | |

*Indicates significant or borderline significant changes from baseline.
[1]Least squares means for change from baseline (BL)|
[2]p = 0.03 and
[3]p = 0.047 using ANCOVA|
[4]Statistically significant or
[5]Trend based on 95% CIs with the upper bound of 0.

Migalastat and Podocyte GL-3.

Figure 4:
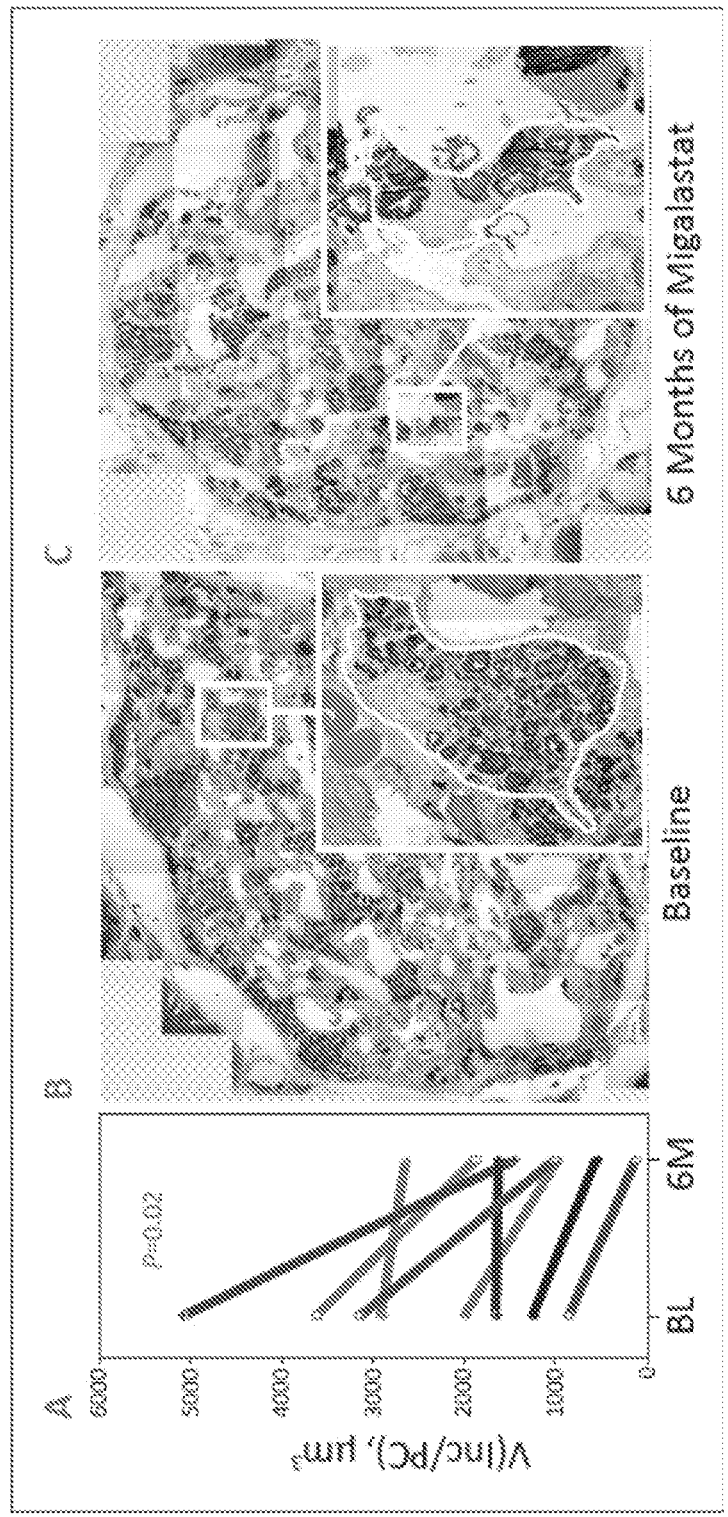
FIG. 4 shows (A) individual changes in GL-3 inclusion volume per podocyte from baseline to after 6 months of migalastat treatment; (B) glomerulus from a patient with Fabry disease at baseline and (C) after 6 months of treatment, as described in Example 1.
Figure 5:
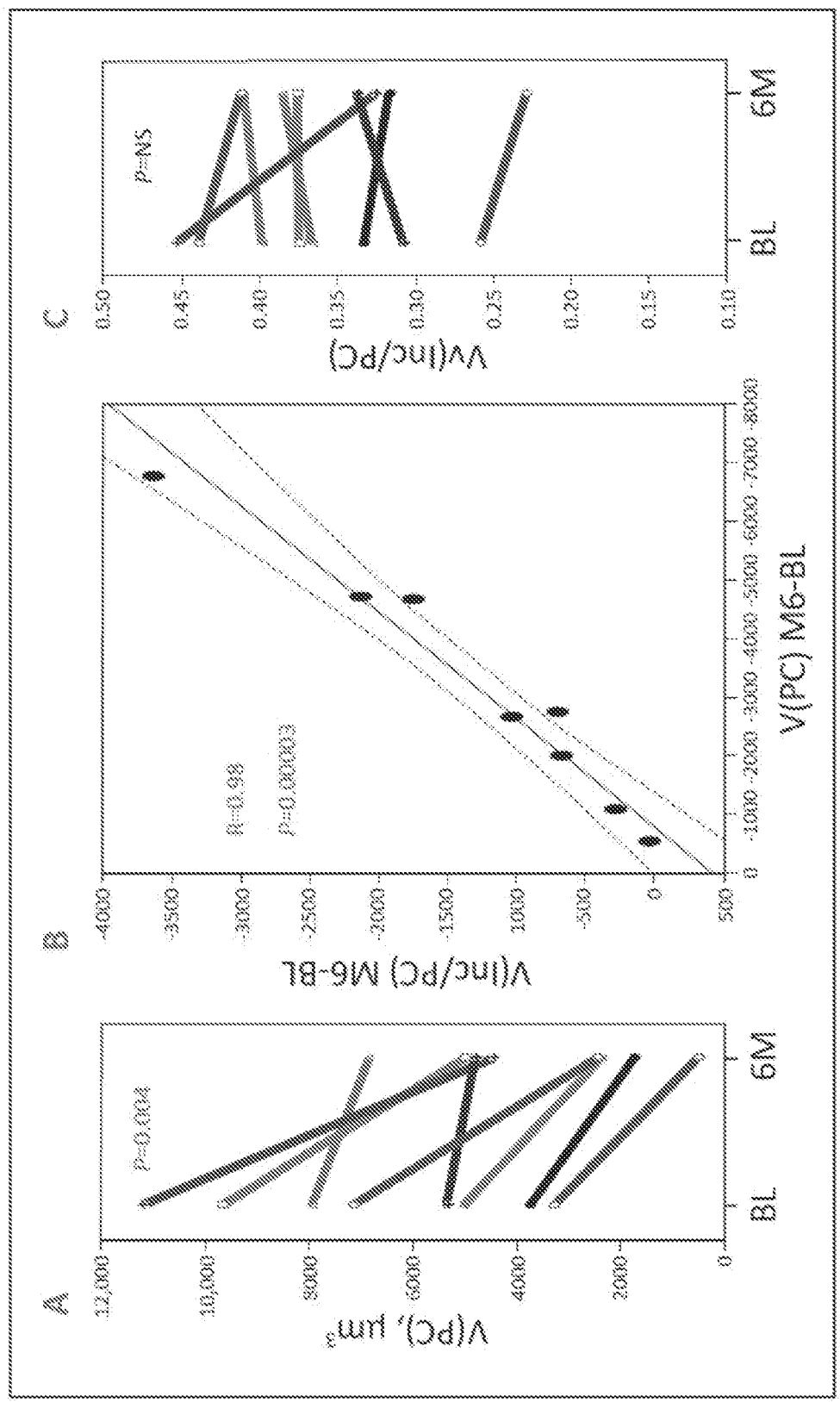
FIG. 5 shows (A) individual changes in podocyte volume from baseline to after 6 months of migalastat treatment; (B) correlation between podocyte volume and podocyte inclusion volume after 6 months of treatment; (C) volume fraction of GL-3 inclusions in podocytes (podocyte inclusion volume/podocyte volume) at baseline and after 6 months of treatment, as described in Example 1.
Figure 6:
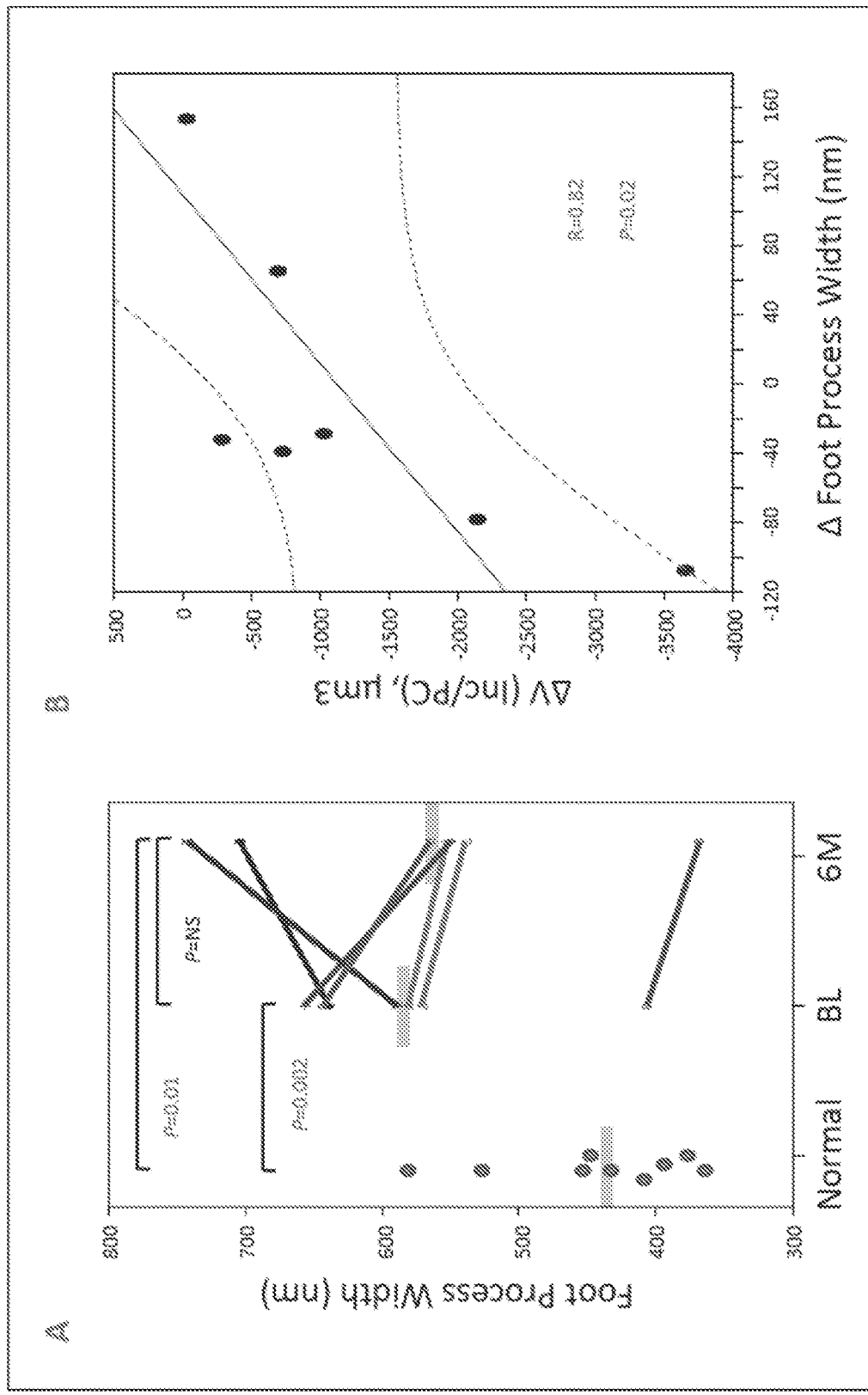
FIG. 6 shows (A) average foot process width in patients with Fabry disease at baseline or after 6 months of migalastat treatment compared with 9 healthy controls; (B) correlation between change in foot process width and change in GL-3 inclusions volume per podocyte, as described in Example 1.
Figure 7:
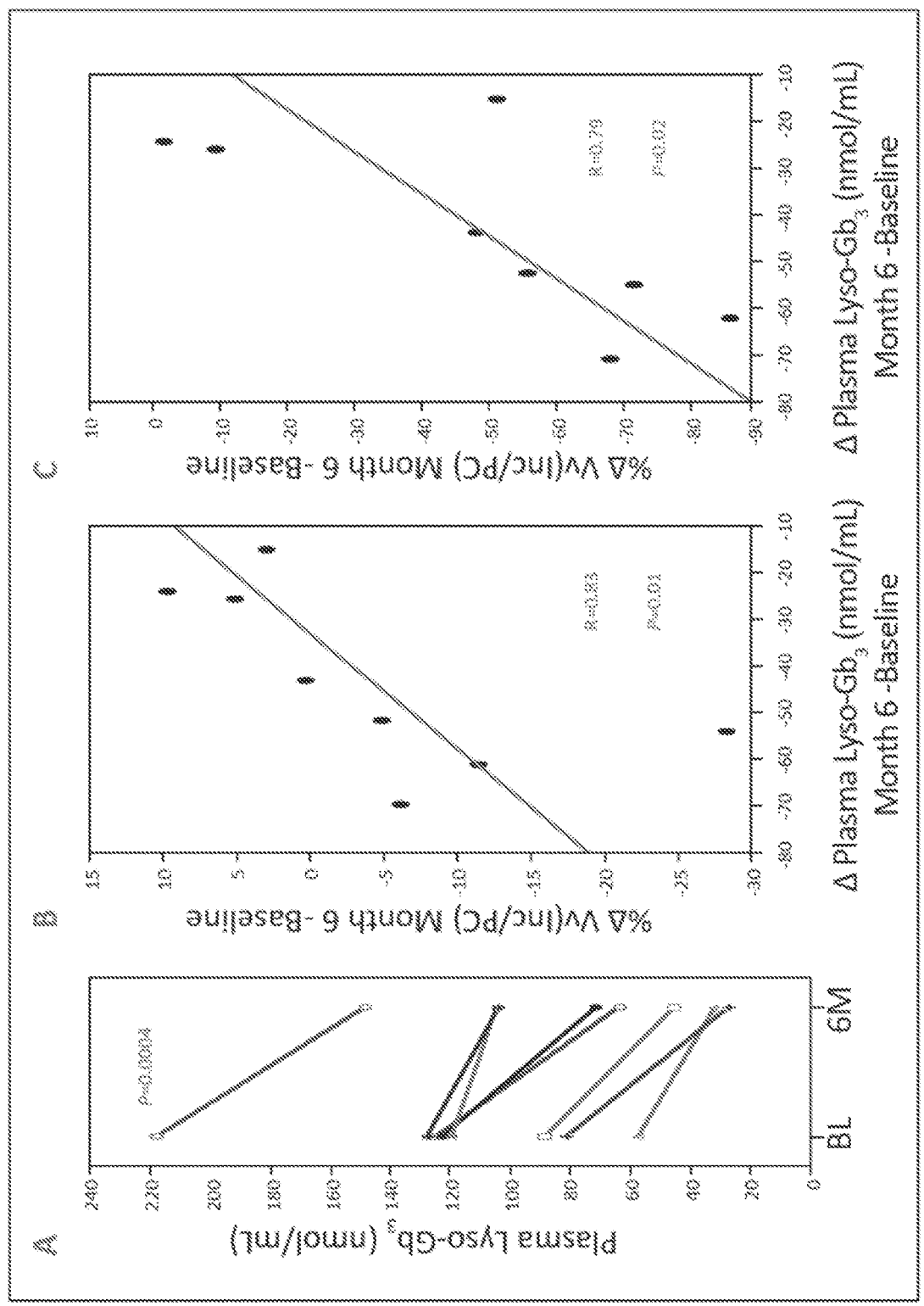
FIG. 7 shows (A) individual changes in plasma lyso-Gb3 from baseline to after 6 months of migalastat treatment; individual comparisons between changes in plasma lyso-Gb3 with (B) changes in volume fraction of GL-3 inclusions in podocytes and (C) changes in GL-3 inclusion volume, as described in Example 1.
Figure 8:
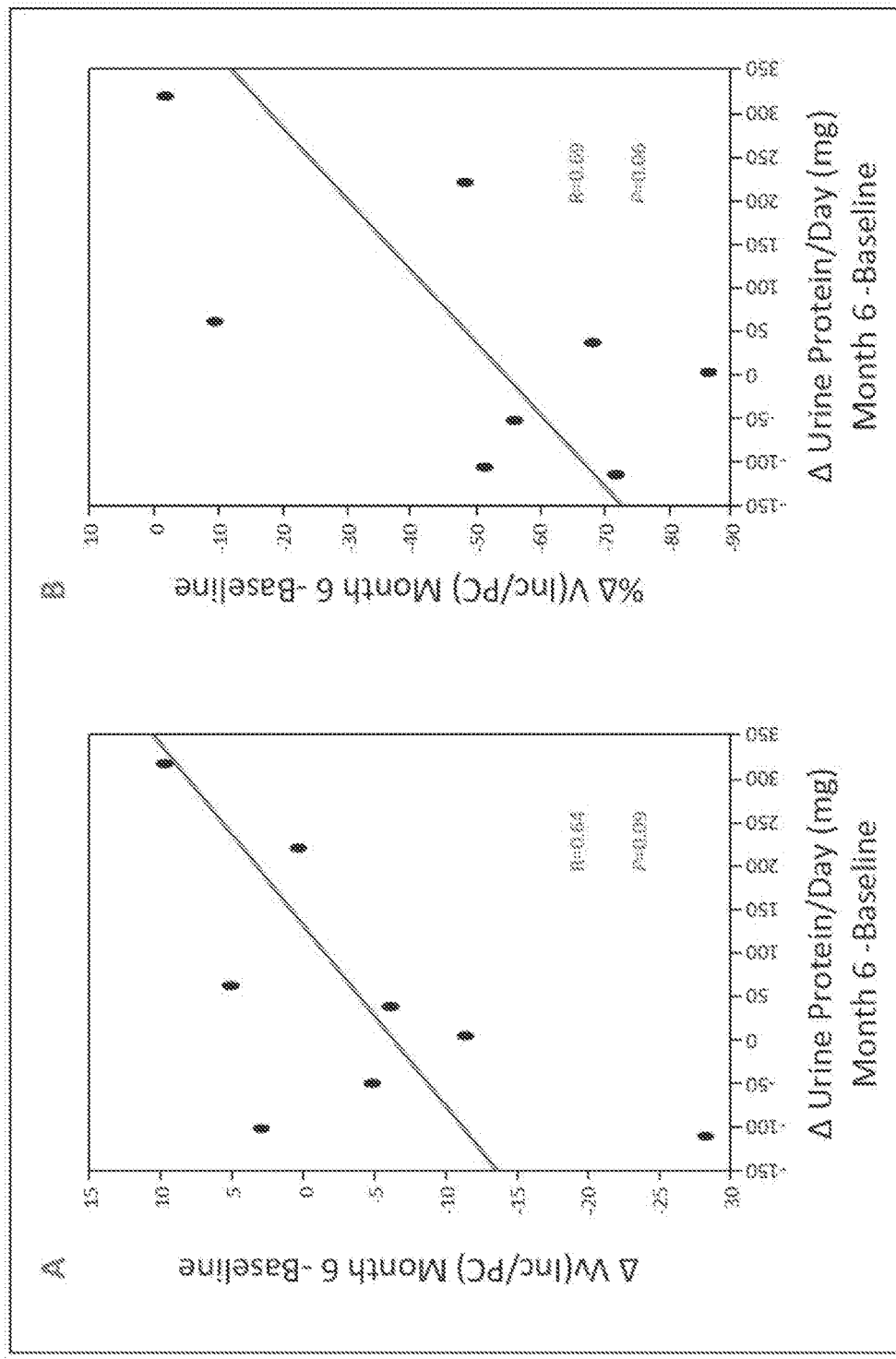
FIG. 8 shows independent comparisons of change in 24-hour urine protein with (A) change in volume fraction of GL-3 inclusions in podocytes and (B) GL-3 inclusion volume, as described in Example 1.

Kidney biopsy samples from ERT-naïve male patients with Fabry disease with GLA mutations amenable to migalastat (N=8), taken at baseline and again after 6 months of migalastat treatment, were studied by masked unbiased electron microscopy stereology. The mean±SD total volume of GL-3 inclusions per podocyte V(Inc/PC) of all patients decreased from 2568±1408 μm³ at baseline to 1282±792 μm³ after 6 months of migalastat (p=0.0182), as shown in FIG. 4. Thus, the reduction in V(Inc/PC) was approximately 50%. There was a correlated reduction in mean podocyte volume from 6680±2835 μm³ at baseline to 3525±2084 μm³ (p=0.004) after 6 months of migalastat (r=0.98, p=0.00003), as shown in FIG. 5. Thus, the reduction in mean podocyte volume was approximately 47%. These findings indicate that the podocyte cytoplasmic shrinkage was proportional to GL-3 loss; thus, the volume fraction of podocyte cytoplasm attributable to GL-3 did not change significantly. The magnitude of podocyte GL-3 volume reduction following migalastat correlated with improvement of foot process width (r=0.82, p=0.02), as shown in FIG. 6. Mean plasma lyso-Gb3 also decreased from 118±48 nM at baseline to 75±42 nM after 6 months of migalastat (p=0.0004), as shown in FIG. 7. This decrease correlated with the percent reduction in podocyte GL-3 volume (r=0.79, p=0.02). There was a trend between decrease in podocyte GL-3 volume and proteinuria (r=0.69, p=0.06) following treatment with migalastat for 6 months as shown in FIG. 8, but no association was found with glomerular filtration rate. In this study, migalastat treatment was associated with a loss of GL-3 inclusions in podocytes in patients with Fabry disease. The sensitive quantitative method used can assess treatment efficacy for this important cell type over a relatively short period of time. This methodology is also more sensitive than other methodologies, including the methodologies used previously in Phase 2 studies and the first methodology described earlier in this example relating to qualitative assessment of podocyte GL-3.

Safety and Adverse Events.

During Stage 1, the treatment-emergent adverse events were similar between groups. Adverse events with a higher frequency in patients receiving migalastat compared to placebo were headache (12/34 patients—35% versus 7/33 patients—21%) and nasopharyngitis (6/34 patients—18% versus 2/34—6%). The most frequently reported adverse events for Stage 2 were headache (9/63 patients—14%) and procedural pain (7/63 patients—11%—related to kidney biopsies) and, for the open-label-extension, proteinuria (9/57 patients—16%), headache (6/57 patients—11%), and bronchitis (6/57 patients—11%). Most adverse events were mild or moderate in severity. No adverse events led to migalastat discontinuation.

Six patients experienced serious adverse events during Stage 1 (2: migalastat; 4: placebo), 5 during Stage 2, and 11 during the open-label-extension. Two serious adverse events were assessed as possibly related to migalastat by the investigator—fatigue and paresthesia. Both occurred in the same patient between months 12-24 and resolved. No individual serious adverse event was reported by >1 patient. Two patients discontinued migalastat due to serious adverse events; both were deemed unrelated to migalastat. No deaths were reported.

Treatment-emergent proteinuria was reported in 9 patients (16%) between months 12-24, and in one case, was judged as migalastat-related. In 5 patients, the 24-month values were in the same range as baseline. Three patients with suitable mutations had overt baseline proteinuria (>1 g/24-hr), which increased over 24 months. In 23/28 patients with baseline proteinuria <300 mg/24-h, 24-hour urine protein remained stable during migalastat treatment.

There was no progression to end-stage renal disease, no cardiac death and no stroke as defined in Banikazemi et al. There was a single case of transient ischemic attack-judged unrelated to migalastat.

Analyses of vital sign, physical findings, laboratory, and ECG parameters did not reveal any clinically relevant effect of migalastat.

Example 2: Dosing Regimens for the Treatment of ERT-Experienced Fabry Patients Using Migalastat Hydrochloride This example describes a Phase 3 study of migalastat therapy in ERT-experienced Fabry patients.

Patient Enrollment.

Eligible patients were 16-74 years old and had genetically-confirmed Fabry disease; had received ERT for ≥12 months; had a GLA mutation that resulted in a mutant protein that would respond to migalastat, based on the human embryonic kidney-293 (HEK) assay used at the time of enrollment; had an eGFR ≥30 ml/minute/1.73 m$^2$; and had an ERT dose level and regimen that had been stable for at least 3 months.

Study Design.

Following eligibility-baseline assessments, 57 patients were randomized to 18 months of migalastat therapy or ERT, followed by followed by 12 months of migalastat therapy. The migalastat dosing regimen was 150 mg of migalastat hydrochloride every other day. The primary objective was to compare the effect of migalastat to ERT on renal function assessed by mGFR$_{iohexol}$ after 18 months of treatment. The secondary objectives were to compare the effect of migalastat to ERT on: renal function (assessed by eGFR and 24-hour urine protein); composite clinical outcome (assessed by time to occurrence of renal, cardiac, cerebrovascular events or death); cardiac function (assessed by echocardiography) and patient reported outcomes (pain and quality of life).

Results

Migalastat and Echocardiographic Parameters.

This study of ERT-experienced patients found that migalastat therapy reduced LVMi. At month 18, mean changes from baseline were −6.6 g/m$^2$ (95% CI −11.0, −2.1; n=31) with migalastat and −2.0 g/m$^2$ (95% CI −11.0, 7.0; n=13) with ERT. In patients with LVH at baseline, the change in LVMi from baseline to month 18 was −8.4 g/m$^2$ (95% CI: −15.7, 2.6; n=13) for migalastat and 4.5 g/m$^2$ (95% CI: −10.7, 18.4; n=5) for ERT.

Patients treated with migalastat continued to show reductions in LVMi at month 30 (−3.8 g/m$^2$ [95% CI −8.9, 1.3]; n=30). Greater reductions were seen in patients with baseline LVH (n=13), with a change from baseline of −9.0 g/m$^2$ after 30 months of migalastat therapy. Among the Fabry patients with baseline LVH, 85% (11/13) had reductions and 31% (4/13) had normalizations of LVMi after 30 months of migalastat therapy.

Example 3: Comparison of Migalastat Dosing Regimens for the Treatment Fabry Disease This example describes a series of Phase 2 studies of migalastat therapy in Fabry patients.

A range of doses and regimens were explored in five Phase 2 studies in 27 subjects (18 males and 9 females):

Twice per day (BID) dosing of 25, 100, and 250 mg of migalastat hydrochloride;

Once per day (QD) dosing of 50 mg of migalastat hydrochloride;

Every other day (QOD) dosing of 50, 150, and 250 mg of migalastat hydrochloride; and 3 days on 4 days off dosing of 250 and 500 mg of migalastat hydrochloride.

In all, 9 different combinations of dosing amounts and dosing schedules were investigated in these Phase 2 studies. Fabry disease is a rare genetic disease, and due to the limited patient population and study sample size for this orphan disease, some of these doses and regimens explored were compared within or across subjects, while others were compared across studies. These five Phase 2 studies were designed to assess the safety, pharmacokinetics and pharmacodynamics of migalastat hydrochloride, with a focus on measures of white blood cell (WBC) α-Gal A activity and urine GL-3 reduction to assess the efficacy of different doses and regimens. WBC α-Gal A activity provides a repeatable, minimally invasive measure of the magnitude of enzyme activity increase associated with different doses of migalastat hydrochloride, and was correlated with less frequently assessed, invasive measures of enzyme activity in skin and kidney. Urine GL-3 provides a repeatable, minimally invasive measure of GL-3 breakdown within lysosomes, the penultimate step in the mechanism of action pathway.

Figure 9:
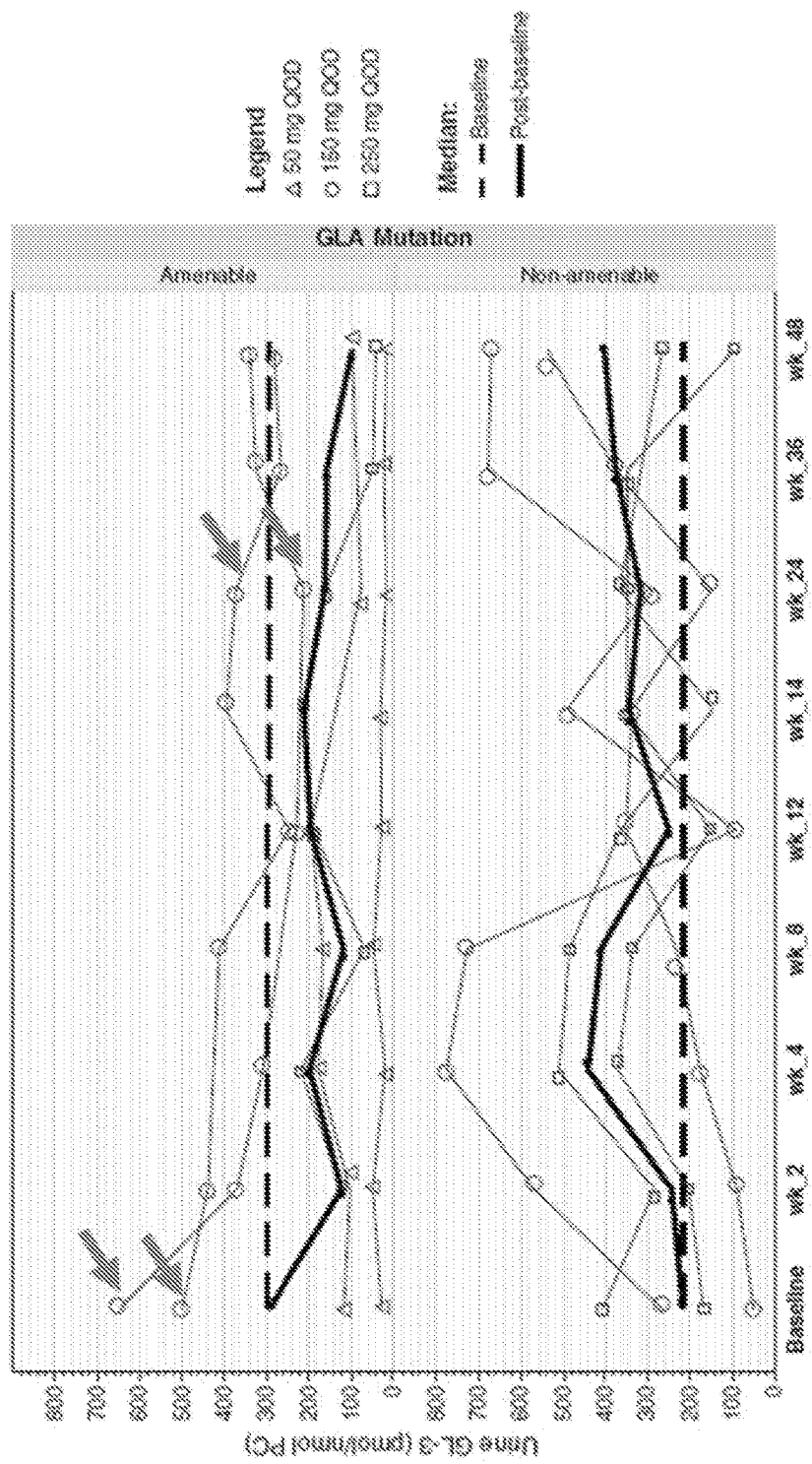
FIG. 9 shows the urine GL-3 levels in female patients on migalastat therapy, as described in Example 3.
Figure 10:
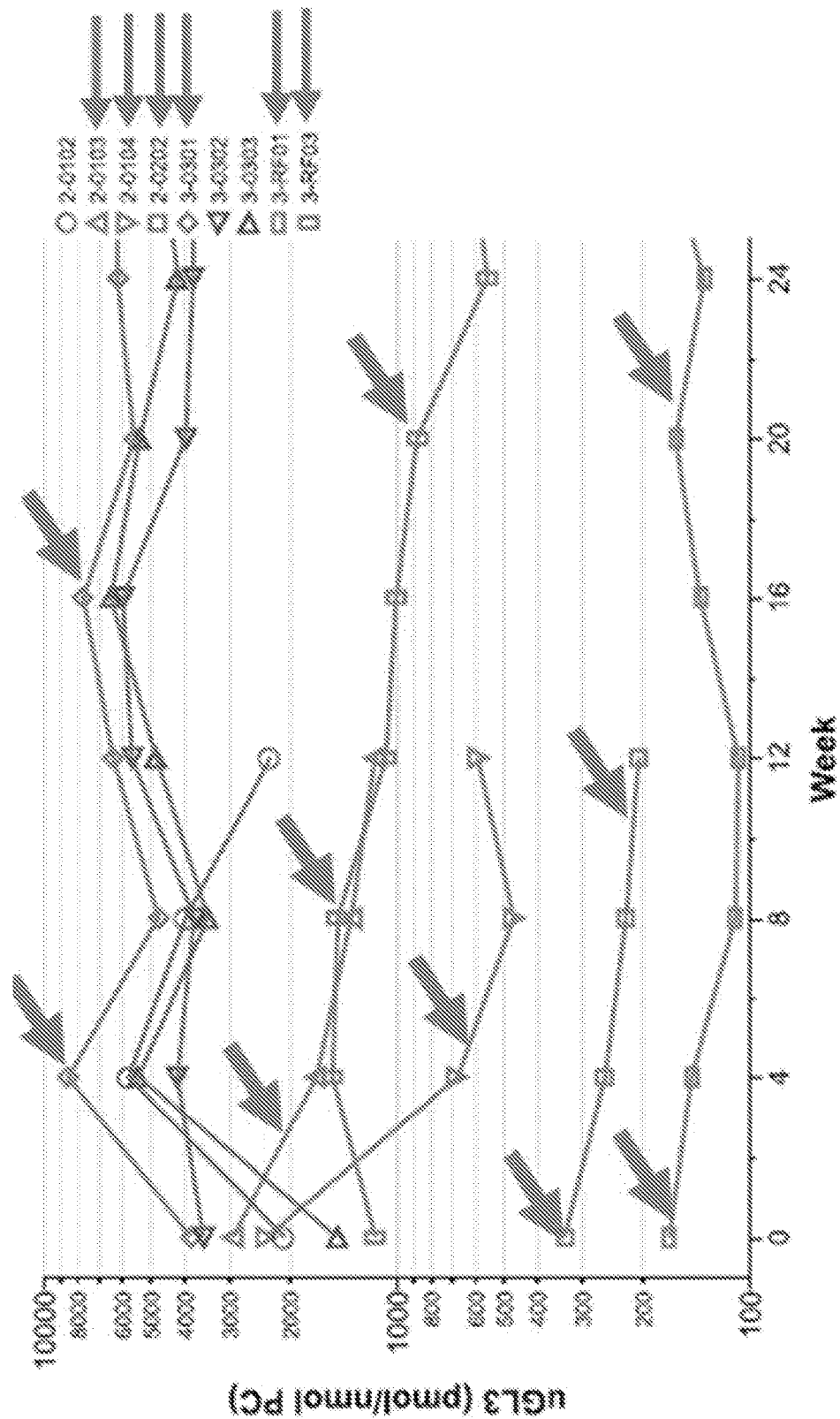
FIG. 10 shows the urine GL-3 levels in male patients on migalastat therapy, as described in Example 3.

In these Phase 2 studies, 150 mg every other day (QOD) resulted in the largest reductions in urine GL-3 in subjects with migalastat-responsive mutations and was generally well tolerated. The urine GL-3 levels for the QOD regimens are shown in FIGS. 9 and 10, and the 8 patients that were on the 150 mg QOD regimen and that had amenable mutations based on the HEK-293 cell-based assay are indicated by the arrows.

In one of the Phase 2 studies, patients were administered migalastat hydrochloride according to the following dosing schedule: 25 mg BID for the first two weeks; 100 mg BID for weeks 2-4; 200 mg BID for weeks 4-6; 25 mg BID for weeks 6-12; and an optional extension of the study at 50 mg per day dosing until up to week 96. The urine GL-3 results from this study are shown in Table 5 below.

TABLE 5

Urine GL-3

| | Total$^a$ Urine GL-3, pmol/nmol PC | | | | | | | |
|---|---|---|---|---|---|---|---|---|
| | Baseline | Week 2 | Week 4 | Week 6 | Week 12 | Week 24 | Week 48 | Week 96 |
| | | | | ATI00I dose: | | | | |
| | 0 | 25 mg BID | 100 mg BID | 250 mg BID | 25 mg BID | 50 mg QD | 50 mg QD | 50 mg QD |
| 01-01 | 66.5 | 72.7 | 155.5 | 371.0 | 54.2 | 55.5 | 50.8 | 52.1 |
| 01-02 | 49.4 | 38.1 | 71.7 | 107.1 | 47.8 | 61.0 | 63.5 | 39.4 |
| 01-03 | 64.1 | 61.4 | 93.7 | 110.2 | 106.3 | 68.2 | 49.3 | 68.3 |
| 01-04 | 159.0 | 198.8 | 272.4 | 556.4 | 140.2 | 139.1 | 120.6 | 131.6 |
| 01-05 | 75.5 | 69.4 | | | | | | |

TABLE 5-continued

Urine GL-3

Total[a] Urine GL-3, pmol/nmol PC

| | Baseline | Week 2 | Week 4 | Week 6 | Week 12 | Week 24 | Week 48 | Week 96 |
|---|---|---|---|---|---|---|---|---|
| | | | | | ATI00I dose: | | | |
| | 0 | 25 mg BID | 100 mg BID | 250 mg BID | 25 mg BID | 50 mg QD | 50 mg QD | 50 mg QD |
| 01-06 | 851.9 | 1641.3 | 2062.3 | 1816.0 | 1914.0 | 1669.2 | 1750.6 | 2266.5 |
| 02-04 | 2212.3 | 3508.8 | 2625.8 | 1845.5 | 469.9 | 1435.0 | | |
| 02-05 | 4091.0 | 2653.0 | 2575.9 | 1784.9 | 1368.9 | 1290.8 | | |
| 03-05 | 457.7 | 800.5 | 619.7 | 984.6 | 1859.7 | | 2647.6 | 2160.8 |

PC = phosphatidylcholine.
[a]Total represents the sum of the five isoforms of GL-3 measured.

Twice-daily dosing at 25, 100 and 250 mg resulted in increases in α-Gal A activity. An increase in α-Gal A activity would be expected to have a positive treatment effect (such as a reduction in build-up of enzyme substrate GL-3). Unexpectedly, Table 5 above shows that there were urine GL-3 increases in a majority of subjects on the BID regimen, which indicates a possible negative effect. This increase in urine GL-3 was possibly due to the high frequency dose interval. When these subjects on a BID regimen were switched to 50 mg per day, some patients demonstrated reductions in urine GL-3, but results were not consistent across all patients. Although pharmacokinetic modelling indicated the 50 mg per day dose should provide exposure troughs below $IC_{50}$ (i.e. below inhibition), urine GL-3 was not as consistently reduced as it was with 150 mg QOD As can be seen by comparing FIGS. 9 and 10 with Table 5, 150 mg QOD provided much larger and more consistent declines in urine GL-3 than dosing every day or twice a day.

A further study was intended to explore the possibility that less-frequent administration of higher doses of migalastat may provide greater substrate reduction than a 150 mg every other day regimen. Subjects were switched from 150 mg migalastat hydrochloride QOD to 250 mg administered once daily for 3 consecutive days ("on drug" period), followed by 4 days without dosing ("off drug" period) for 8 weeks and then 500 mg (3 days on, 4 days off) for at least 8 weeks. A few subjects showed an increase in WBC α-Gal A levels at the higher doses; however, some subjects also showed signs of increases in urine GL-3. As illustrated in Table 6 below, mean and median urine GL-3 levels increased after subjects were switched from 150 mg QOD to 250 and 500 mg 3 on 4 off. Mean and median urine GL-3 then went back down when subjects were switched back to 150 mg QOD. Additionally, a few subjects did not tolerate the higher doses.

TABLE 6

Urine GL-3
Study Fab-205 Urine GL-3 Results (preliminary)

| DEP Visit 1 | | |
|---|---|---|
| n | 12 | All Amenable |
| Mean (SD) | 342.069 (531.1137) | subjects on 150 mg |
| Median | 77.71 | QOD |
| Min, Max | 30.68, 1538.33 | |

TABLE 6-continued

Urine GL-3
Study Fab-205 Urine GL-3 Results (preliminary)

| DEP Visit 4 | | |
|---|---|---|
| n | 16 | All Amenable |
| Mean (SD) | 520.027 (690.3037) | subjects after |
| Median | 168.85 | switching to 250 mg |
| Min, Max | 28.96, 2503.34 | 3 on 4 off for 8 wks |
| Visit 6 | | |
| n | 15 | All Amenable |
| Mean (SD) | 937.733 (1502.4504) | subjects after |
| Median | 321.70 | switching to 500 mg |
| Min, Max | 30.10, 5561.42 | 3 on 4 off for 8 wks |
| Visit 10 | | |
| n | 13 | All Amenable |
| Mean (SD) | 659.829 (1054.5852) | subjects after |
| Median | 278.06 | being on 500 mg |
| Min, Max | 41.68, 3976.42 | 3 on 4 off for >1 year |
| Visit 14 | | |
| n | 11 | All Amenable |
| Mean (SD) | 354.549 (483.1105) | subjects after |
| Median | 111.62 | switching back |
| Min, Max | 32.86, 1418.94 | to 150 mg QOD for 3-6 months |
| Visit 18 | | |
| n | 11 | All Amenable |
| Mean (SD) | 609.767 (782.6499) | subjects after |
| Median | 177.31 | being back on |
| Min, Max | 52.76, 2445.41 | 150 mg QOD for >1 year |

Based on the results of these studies, dosing every other day provides unexpected benefits that are not present with either daily or twice daily dosing. In particular, dosing every other day in resulted in the most consistent reductions in urine GL-3 in subjects with migalastat-responsive mutations. Indeed, many of the other dosing regimens actually lead to increases in urine GL-3. Dosing every other day also led to a more consistent decrease in urine GL-3 than 3 days on 4 days off dosing, and some of these patients on the 3 days on 4 days off dosing also showed an increase in urine GL-3. Returning to 150 mg QOD after the 3 days on 4 days off dosing lowered the mean and median urine GL-3 levels.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

Patents, patent applications, publications, product descriptions, GenBank Accession Numbers, and protocols are cited throughout this application, the disclosures of which are incorporated herein by reference in their entireties for all purposes.

What is claimed is:

1. A method of reducing gastrointestinal symptoms in a Fabry patient exhibiting one or more gastrointestinal symptoms, the method comprising administering to the patient a formulation comprising an effective amount of migalastat or salt thereof every other day to thereby reduce one or more of the gastrointestinal symptoms, wherein the effective amount is about 123 mg free base equivalent (FBE), wherein the gastrointestinal symptoms comprise diarrhea, wherein the patient is an enzyme replacement therapy (ERT)-naïve patient and wherein the patient has a mutation in α-Galactosidase A selected from the group consisting of A156T, D33G, G144V, and M187I.

2. The method of claim 1, wherein administration of migalastat or a salt thereof for at least 18 months to an enzyme replacement therapy (ERT)-naïve patient having diarrhea symptoms at baseline provides a decrease in diarrhea of greater than 1.0 as assessed using the Gastrointestinal-Symptoms-Rating-Scale (GSRS).

3. The method of claim 1, wherein the patient is administered about 123 mg of migalastat free base every other day.

4. The method of claim 1, wherein the patient is administered about 150 mg of migalastat hydrochloride every other day.

5. The method of claim 1, wherein the formulation comprises an oral dosage form.

6. The method of claim 5, wherein the oral dosage form comprises a tablet, a capsule or a solution.

7. The method of claim 1, wherein the migalastat or salt thereof is administered for at least 6 months.

8. The method of claim 1, wherein the migalastat or salt thereof is administered for at least 18 months.

9. A method of reducing gastrointestinal symptoms in a Fabry patient exhibiting one or more gastrointestinal symptoms, the method comprising:
   (i) identifying an enzyme replacement therapy (ERT)-naïve patient having Fabry disease and exhibiting diarrhea, reflux, and indigestion, and
   (ii) administering to the patient migalastat or salt thereof every other day in an amount effective to reduce the diarrhea, reflux, and indigestion, wherein the effective amount is about 123 mg free base equivalent (FBE), wherein the patient has a mutation in α-Galactosidase A selected from the group A156T, D33G, G144V, and M187I, wherein the administration results in (a) a decrease in diarrhea of greater than 1.0 as assessed using the Gastrointestinal-Symptoms-Rating-Scale (GSRS), (b) a decrease in reflux of greater than 0.6 as assessed using the GSRS, and (c) a decrease in indigestion of greater than 0.5 as assessed using the GSRS.

10. The method of claim 9, wherein the mutation is D33G.

11. The method of claim 9, wherein the mutation is M187I.

12. The method of claim 1, wherein the mutation is A156T.

13. The method of claim 1, wherein the mutation is D33G.

14. The method of claim 1, wherein the mutation is G144V.

15. The method of claim 1, wherein the mutation is M187I.

16. The method of claim 9, wherein the mutation is A156T.

17. The method of claim 9, wherein the mutation is G144V.

\* \* \* \* \*

SEQUENCE LISTING

```
<160> NUMBER OF SEQ ID NOS: 2

<210> SEQ ID NO 1
<211> LENGTH: 12436
<212> TYPE: DNA
<213> ORGANISM: Homo sapiens

<400> SEQUENCE: 1
cccttctgta ggggcagaga ggttctactt cattactgcg tctcctggga aggccatcag      60
gactgctggc taaagtggga accaggactc tttgtgagtt aagaatttgt gtatttatat     120
gtgtgttata cacattttt aaaaaactgt aacgacatca ggttgagcag tcgtctccgg      180
gtggtgaatt atgtgtattt ttaaatttta tactatattg ttattttca aatgttcgaa      240 attgaatatg tagattgttg ttatcagcag aaaaataaac attattcaaa tactctattc     300
agtaaagtaa tttattgggc gcctttgtca agcacgcatt tgcctagatg tgactctaca     360
gataaaattc acttggggcc tccccttaca gacaatcagg cagtggagac tgagtgcctg     420
aatggataga ccagcactca gaccactatt ttcagtatct gttttttctta actcagggcc     480 gtggttttca aacgttttc gccttacggt caccttagg gtccccgag accggcccag       540 acagacagat atacaaaaac acatacacag tcatgagcgt ccaccatttc cccaccaggc     600
gcagcacagg cggcttccg gcactgagat gggggggagg agggagagag cgcgaggggg     660 gagggaaag cagagaacga aagaggcgga ggcggccccc gaacccgct ctggtcttca      720 tcatcaccac ccctgggtcc ccagttccca cccacacacc aacctctaac gataccgggt     780
aattttcctc cttcttccct caaacggcta tagcgagacg tagacgacg accagaacta      840 cttctgctca cgtaagcgag taatcacgtg agcgcctacg tcatgtgaga tctcggtcac     900
gtgagcaact ctcggcttaa actcgggatc actaaggtgc cgcacttcct tctggtatgg     960
aaatagggcg ggtcaatatc aagaaggaa gagggtgatt ggttagcgga acgtcttacg    1020
tgactgatta ttggtctacc tctggggata accgtcccag ttgccagaga aacaataacg    1080
tcattattta ataagtcatc ggtgattggt ccgcccctga ggttaatctt aaaagcccag    1140
gttacccgcg gaaatttatg ctgtccggtc accgtgacaa tgcagctgag gaacccagaa    1200
ctacatctgg gctgcgcgct tgcgcttcgc ttcctggccc tcgtttcctg ggacatccct    1260 gggctagag cactggacaa tggattggca aggacgccta ccatgggctg gctgcactgg     1320
gagcgcttca tgtgcaacct tgactgccag gaagagccag attcctgcat caggtatcag    1380
atattgggta ctcccttccc tttgcttttc catgtgtttg ggtgtgtttg gggaactgga    1440
gagtctcaac gggaacagtt gagcccgagg gagagctccc ccacccgact ctgctgctgc    1500 tttttatcc ccagcaaact gtcccgaatc aggactagcc ctaaactttc tctgtgtgac     1560
ctttcctggg atgggagtcc ggccagcggc cctgttttct ttctctctct ctctctctct    1620
cgttctcctt ctctttctct ttctcttctt tcctctctct ttctctctct ccctgcccgg    1680
```

-continued

```
ttctctttt tcactgctcc ttgcagagca gggccacccc ataggcagtg tgcccaaagt    1740
agccctgccc ggttctattc agacccttct tgtgaacttc tgctcttcct ctgccgggtg    1800
ctaaccgtta gaacatctag ggtgggtagg aggaatgggg aactaagatt cgtgccattt    1860
tttctccttt tggggtcgtg gatttctcgg cagtatctcg agggagttag agagaccata    1920
aggtcgctga gatctctccc acctcgccca tgagcgtggc atcaggctgg aaggttgaca    1980
tggaggaact ttatacattt acccttttgc gtgagggttg aggctggatt agataggtat    2040
tgaacatatc tgaccctcac aatccttatc tgtaaattgg gattacaacc ttttaatttc    2100
agggagctga caaaaaaaat ctgaaaaata gttcttatct cacacaggtg agttttcaag    2160
gagataacct atttaaagta catagcacag cgcttgacca ttcaactgcg cttacagagc    2220
aaatgttcaa tgggaaaatg aatgtaaatc tacaaatctg aatgaatatg tgtattttc     2280 tggagagagg atatttacct ttcttcaaat tctcaagggg ctctgtgatt taaaaaaggt    2340
taggaatcac tgatagatgt tggtaaaagg tggcagtcac agtacatttc tgtgtccata    2400
agttattcct atgaatatct ttatagataa agtcaggatg ttggtcagac atcacagaag    2460
aaattggcct tgtaagtttc atgtgaccct gtggtacagt atgtgtggca attttgccca    2520
tcacggattt ttttttattg gtatttgcat ctgattataa aactaatgca tgatcattgc    2580
aaaaaatgta gataaagaag agcaaaatga aaataaagat tccccccac cgttccacca     2640 cccagaaata atcatggttt aaatgttaat atacaacctt acaattgttt tctatataaa    2700
tgaaaacata gatttccttta tttcattatt ttccataaaa aatggatcat gtttatgtca    2760
tgtttggcta atggcaagac cctggcaccc agtctgggct caaattctgc ctcattgtta    2820
cttagccctg tgacattggg taaattacac tttttttttt tttttttttt tgagacgggg    2880
tctcgctctg tcgcccaggc tggagtgcag tggcacgatc tcggctcact gcaagtccgc    2940
ctcctgggtt cacgccattc ttctgcctca gcctcccgag tagctgggac tacaggcgcc    3000
tgccaccacg cctggctctt ttttttttt ttttttttt tagtacagac ggggtttcac    3060
catgttagcc agggtggtct caatctcctg acctcgtgat tcgcccgcct cagcctccca    3120
aagtgctggt gtgagccacc gtgcccagcc ttacttttt ttttgagagg gggtctcact     3180
ctgtcaccca ggttggagtg cagtggcgcg atctctgctc agtgcaaact ccacctcccg    3240
ggtttaagca gttctcctgt cgtagtctcc tgagtagctg ggattacagg cacaccacca    3300
cggccagcta atttttgtat tttcagtaga gacgggtttc accatgttgc ccaagctggt    3360
ctcgaactcc tggcctcaag tgatctgccc gccttggcct cccagagtgc tgggattaca    3420
ggtgtgagcc accgcacccg gcctcttttt tcttttttag tctatcatac cttgcaaata    3480
cagtggttct tcctatgtgt tggttttgat atttatgtaa tcaaacacat cagttttcc     3540 tttctgattt ctgactttgg ggtcatgctg agaaagtcct ttcctacctg aagataatac    3600
agtatatacg tttcttacta gtattttgt ggattttaa aatatttaaa tctttagtcc      3660
atctgaactt gttcttctat cagaaatgcc acatttaata aataataagt cccatggtat    3720
cagatggctg gaaggacctc tttcgaaact ttgtttaatt ccattaatct gtgtattctt    3780
attctaatgc taatagttcc acactagctt cctttatctt ttttttcttt tttttttttt   3840
ttttgagctg gagtttcgct cttgttgccc aggctggagt acaatgtcac gatctcggtt    3900
caccgcaacc tccgcctccc aggttcaagc aattctcctg cctcatcctc gcgagtagct    3960
ggaattacag gcatgcgcca ccacgcctag ctattttgta tttttagtag agatggggtt    4020
tctccatgtt ggtcaggctg gtctcaaact cccagcctca ggtgatctgc ctgcctcggc    4080
```

```
ctcccaaaat gctgttatta caggcgtgag ccaccacgcc cagccttcat cttttaatga   4140
atgtacatgt atgtaatctt ttaggtgaac tttttgtaat gttgtgccaa gttccttaaa   4200
aagcccsttt ggaagctggg caggtggcca cgcctgtaat cccagcattt tgggagtctg   4260
aggcaggtgg atcacttgag gccaggagtt caagactagc ctagccaaaa tgcaaaaccc   4320
tgtctctact aaagatacaa aaattagccg gatgcgatgg cacatgcctg taatctcagc   4380
tactcgggag gctgaggtag aagaatcgct tgaaccgggg aggcagaggt tgcagtgagc   4440
aagatggcgc cactgcactc cagcctgggt gacagaggga gactccatct caaaaaaaaa   4500
aaaaaaaaaa aagataaaaa ggaaacctaa gtactcttgg gctttgttaa ggattttgtt   4560
aaatatacaa aggattgcag ggaaaattaa cttatttta atattgagta tgcttatcca   4620
agagcaaaat aatatttctc catttattca aatcatttag gagcatcata gttttaacat   4680
atgggccttg cacgtatctt aaatttatct ctaggcattt taggttgttc agttgttctt   4740
gtgaatggga tctttttctc caaataggat tattgttgat atctgttgat tatgttaact   4800
ttgtagtttc tgactttact gaactgtctt cttagatcta atactctttt caatttcatc   4860
atatatttct cattcctatt ttgtttgggg tttttagggc gggaatatta acgggataag   4920
agagacaaaa gaaaatctgg aaaaacaatt cattttacct tacattgctt gtgattacta   4980
ccacactatt actgggttgg aaaaaattgt gaaatcccaa ggtgcctaat aaatgggagg   5040
tacctaagtg ttcatttaat gaattgtaat gattattgga atttctcttt cagtgagaag   5100
ctcttcatgg agatggcaga gctcatggtc tcagaaggct ggaaggatgc aggttatgag   5160
tacctctgca ttgatgactg ttggatggct ccccaaagag attcagaagg cagacttcag   5220
gcagaccctc agcgctttcc tcatgggatt cgccagctag ctaattatgt gagtttatag   5280
ataatgttct tgttcattca gaggactgta agcacttctg tacagaagct tgtttagaaa   5340
cagccctcat ggccgggcgt ggtggctcac gctgtaatcc caacactttg ggaggccgag   5400
gcgggtggat cacctgaggt caagagttca agaccagcct ggccaacatg gtgaaacccc   5460
aactctatta aaagtacaaa aaattagctg gcatggtgg tgaacgcctg taaccccagc   5520
tacttgggag gctgaggcag gagaatcgct tgaacccagg aggtggaagt ttcagtgagc   5580
tgagatcacg ccattgcact ctagcctggg caacaaaaga gaaactccat ctcaaaaaaa   5640
aaaacaagga aaaaagaaa cagccctcat gacacttaga aagtagaata gctggctgtt   5700
atctgaacat tgaattgtaa ggcttatcag gtggactttg cattccatca gcagacaatt   5760
tttttttttt ttttttttg agatggagtc tcattctgtc tcccaggctg gagggcagtg   5820
gtgcgatctc ggctcactgc aagctccacc tcctgggttc atgccattct cctgcctcag   5880
cctcccaagt agctgggacc acaggcaccc gccaccatgc ccagttaatt ttttgtattt   5940
ttagtagaga cggggtttca ccatgttagc caagatggtc tcgatctcct gacctcgtga   6000
tccgcccacc tcggcctccc aaagtgctgg gattacaggc atgagccacc gcgcctagcc   6060
tacaaatgtt ttgtaatagc tcttgaggcc catcttggag ttctccttt gctaaaacca   6120 ctgaactctc taggaggaaa aaggaacttg gttcttgaca tatgtgtgca tgtatttcca   6180 tataacctttt aggaagctat tgcaatggta ctataaacta gaattttaga agatagaagg   6240
aaaatattct ggagatcatt gaagagaaat ggagtccaac actagttaaa gatgatgaag   6300 acagatttt ttttttgacg gagtctcgct ctgtcgccca ggctggagtg cagtggcaca   6360
atctcagctc actgcaaccc tccacctctt gggttcaagt gattctcctg cctcagcctc   6420
```

-continued

```
ccaagtagct gggactacag gcgcacacca ccacgcccgg ctaattttg tattttagt      6480
agagacaagg tttcaccata ttcgccaggc tggtctcgaa ctcctgacct tgtaatccgc      6540
ccaccttggc ctcccaaagt gctgggatta caggcatgag ccaccacgcc cggccgatga      6600
agacagattt tattcagtac taccacagta gaggaaagag ccaagttcaa ttccaaatac      6660
aacaaagaca ggtggagatt tatagccaat gagcagattg aggggggtcag tggatggaat      6720
atttaagaag acatcaaggg tagggagctt cttgctaaag cttcatgtac ttaaacaaga      6780
agggtggggg atgagggaaa ttgatcagat atcaatggtg gcagtattga cttagcagga      6840
ttcttgctaa gaggtcttgc taggacagac ataggaagcc aaggtggagg tctagtcgaa      6900
aagaaggctc atcagagaag tctaactaaa gtttggtcaa gaagagtctt tgtcaaggta      6960
aatctatcat ttccctcaaa aggtaatttt caggatccca tcaggaagat tagcatggct      7020
gctagctttc tcctcagttc tgggctatag ctcacatgcc tagtttgaac tagctcagca      7080
gaactggggg atttattctt tgtcttccaa caaactcatc tggatgattt tgggggtttg      7140
tggggaaaag cccccaatac ctggtgaagt aaccttgtct cttcccccag cctggaatgg      7200
ttctctcttt ctgctacctc acgattgtgc ttctacaatg gtgactcttt tcctccctct      7260
catttcaggt tcacagcaaa ggactgaagc tagggattta tgcagatgtt ggaaataaaa      7320
cctgcgcagg cttccctggg agttttggat actacgacat tgatgcccag acctttgctg      7380
actggggagt agatctgcta aaatttgatg gttgttactg tgacagtttg gaaaatttgg      7440
cagatggtaa tgtttcattc cagagattta gccacaaagg aaagaacttt gaggccatgg      7500
tagctgagcc aaagaaccaa tcttcagaat tttaaatacc ctgtcacaat actggaaata      7560
attattctcc atgtgccaga gctcccatct cttctctttc agttcattaa ttaattaatt      7620
aattcatgta aaatccatgc atacctaacc atagctaata ttgtgcactt ataattcaag      7680
agggctctaa gagttaatta gtaattgtaa ctctctataa catcatttag gggagtccag      7740
gttgtcaatc ggtcacagag aaagaagcat cttcattcct gcctttcctc aatatacaca      7800
ccatctctgc actacttcct cagaacaatc ccagcagtct gggaggtact ttacacaatt      7860
taagcacaga gcaactgcct gtccctgctg ctagtttaaa catgaacctt ccaggtagcc      7920
tcttcttaaa atatacagcc ccagctgggc atgatggctc atgcctgtaa tcctagcact      7980
ttgggaggct gaggcgggtg gattacttga ggtcaggagt tcgagaccac cctgccaac       8040
atggtgaaac cccatctcta gtaaaaatac aaaaattagc tgactttggt ggcacatgcc      8100
tgtaatccca gctactggg aagctgagac agaagagtca cttgaacctg ggaaacagag       8160
gttgcagtga gccaagatcg caccactgca ctccaccctg gatgacagac tgaaccccat      8220
ctcaaaaaat taaataaaa taaaataaaa taactatata tatagcccca gctggaaatt      8280
catttctttc ccttatttta cccattgttt tctcatacag gttataagca catgtccttg      8340
gccctgaata ggactggcag aagcattgtg tactcctgtg agtggcctct ttatatgtgg      8400
cccttttcaaa aggtgagata gtgagcccag aatccaatag aactgtactg atagatagaa      8460
cttgacaaca aaggaaacca aggtctcctt caaagtccaa cgttacttac tatcatccta      8520
ccatctctcc caggttccaa ccacttctca ccatccccac tgctgtaatt atagcctaag      8580
ctaccatcac ctggaaagtc atccttgtgt cttccccttt atttccaccat tcatgtcctg      8640
tctatcaaca gtccttccac cagtatctct aaaatatctc ctgaatcagc ccacttcctt      8700
ccatcttcac tacatgcacc ctggccttcc aagctactat cggctctcaa ccagactgct      8760
gggaccacct gatctctctg cttccactct gtctcaaccc ccatctattt tccaagcagc      8820
```

```
actagagtta tcatattaaa atgtaaatat cagttttttt tttaaagaaa aaaaccctga   8880
gacttaacag agttataaaa aatataaatg tcatcatcag ttccctgctt aaaacccttg   8940
actcgcttcc aattgcactt ggaatgaaac caaactgcac tgatccagcc cttgcctgcc   9000
tccccaaagt ccaaggggtc atggctcttt ccctggctac actggttttc tttctgtccc   9060
tcaacactgc aagcctattg ctgccccagg gcctttacac ttgcttttt  tctgcctaga   9120 acagttcttc cccaaagatt tttaaagggc cgggctcctt aacattgaag tcgcagacca   9180
aacgccacat atgcagacag ttcttctcta actactttaa aatagccctc tgtccattca   9240
ttcttcatca cattaacctg tttaattttc ttctcagagc tccacactat ttggaagtat   9300
ttgttgactt gttaccatgt ctccccacta gagtgtaagt ttcatgaggg cagggacctt   9360
gtctgacttt gactgtatct ctcgcatatg gttaagtgtt aaatagttat ttatggaatg   9420
aatccctatt attccctcat tatctctgca aaatagtctt ttttctcaac atcttaaacc   9480
tgatatccca cctgcctatc tacaaacttt tttttgcga  cagagtctca ctgtcaccca   9540
ggctagagtg cagtggcgcc atctcggctc actgcaacct ccgcctcccg ggtttaagcg   9600
attctcttgc ctcagcctcc cagtagctgg gattataggc gtgcgctacc acatctggct   9660 aattttgta  ttttagtag  agatggtttc accatgttgg ccaggcttgt ctcgaactcc   9720
tgacctcaga tgatccacct gcctcggcct cccaaagtgc tgggattaca ggcatgagcc   9780
accgtgccca gcctctacaa acttttatt  ccattaacaa actatatgct gggatttaag   9840
ttttcttaat acttgatgga gtcctatgta attttcgagc ttttaatttt actaagacca   9900
ttttagttct gattatagaa gtaaattaac tttaagggat ttcaagttat atggcctact   9960
tctgaagcaa acttcttaca gtgaaaattc attataaggg tttagacctc cttatggaga  10020
cgttcaatct gtaaactcaa gagaaggcta caagtgcctc ctttaaactg tttttcatctc  10080 acaaggatgt tagtagaaag taaacagaag agtcatatct gttttcacag cccaattata  10140
cagaaatccg acagtactgc aatcactggc gaaattttgc tgacattgat gattcctgga  10200
aaagtataaa gagtatcttg gactggacat cttttaacca ggagagaatt gttgatgttg  10260
ctggaccagg gggttggaat gacccagata tggtaaaaac ttgagccctc cttgttcaag  10320 accctgcgt  aggcttgttt cctattttga cattcaaggt aaatacaggt aaagttcctg  10380
ggaggaggct ttatgtgaga gtacttagag caggatgctg tggaaagtgg tttctccata  10440
tgggtcatct aggtaacttt aagaatgttt cctcctctct tgtttgaatt atttcattct  10500
ttttctcagt tagtgattgg caactttggc ctcagctgga atcagcaagt aactcagatg  10560
gccctctggg ctatcatggc tgctccttta ttcatgtcta atgacctccg acacatcagc  10620
cctcaagcca aagctctcct tcaggataag gacgtaattg ccatcaatca ggacccttg   10680 ggcaagcaag ggtaccagct tagacaggta aataagagta tatttttaa  gatggcttta  10740 tatcccaat  accaactttg tcttgggcct aaatctattt ttttcccttg ctcttgatgt  10800
tactatcagt aataaagctt cttgctagaa acattacttt atttccaaaa taatgctaca  10860
ggatcatttt aatttttcct acaagtgctt gatagttctg acattaagaa tgaatgccaa  10920
actaacaggg ccacttatca ctagttgcta agcaaccaca ctttcttggt ttttcaggga  10980
gacaactttg aagtgtggga acgacctctc tcaggcttag cctgggctgt agctatgata  11040
aaccggcagg agattggtgg acctcgctct tataccatcg cagttgcttc cctgggtaaa  11100
ggagtggcct gtaatcctgc ctgcttcatc acacagctcc tccctgtgaa aaggaagcta  11160
```

-continued

```
gggttctatg aatggacttc aaggttaaga agtcacataa atcccacagg cactgttttg    11220
cttcagctag aaaatacaat gcagatgtca ttaaaagact tactttaaaa tgtttatttt    11280
attgccaact actacttcct gtccaccttt ttctccattc actttaaaag ctcaaggcta    11340
ggtggctcat gcctgtaatc ccagcacttt gggaggctga ggcgggcaga tcacctgagg    11400
tcgggacttt gagacccgcc tggacaacat ggtgaaaccc catttctaat aaaaatataa    11460
aaattagcca ggtgtggtgg cgcacctgtg gtcccagcta ctctggggc tgaggcatga     11520
gaatcgcttg aacccgggag tggaggttgc attgagctga gatcatgcca cctcactcca    11580
gcctgggcaa caaagattcc atctcaaaaa aaaaaaaaaa gccaggcaca gtggctcatg    11640
cctggaatcc cagcactttt ggaagctgag gcaggcagat cacttgaggt taggatttca    11700
agaccagcct ggctaacata gtaaagccct gtctctacta aaaatacaaa aattagccag    11760
gtatggtggc gagcttctgt agccccagct actcaggaga ctgaggcagg agaatcactt    11820
gaacccggga gtggggggg tgcagtgacc caagatcacg ccactgcatt ccagcctggg     11880
caacagagca agactccatc tcaaaaaaaa aagttctatt tccttgaata aaattttccg    11940
aagtttaaac tttaggaata aaactattaa acccgtattt actcatccag atacccaccc    12000
cccttgttga gattctctcc caattatcaa aatgtgtagc atatttaact accaagagct    12060
aaacatcatt aagactgaaa tgtattaaga aggatgtata ggccaggcac ggtgtctcac    12120
gcctgtaatc ccaacacttt ggaggccaa gtcgggcgga tcacgaggtc aggagatgga     12180
gaccatcctg gccaacatgg tgaaaccccc tctctactaa aaatacaaaa attagccagg    12240
caggtggcag gcacctgtaa tcccagctac tccagaggct gaggcaggac aatcacttga    12300
acctgggagg cagaggctgc agtgagctga ggttgtacca attgcactcc agcctaggta    12360
acgagcaaca ctccatctca aaaaagaaa aaaaaaaga tgtataattt ggaactgtta      12420
agaggcattt taaaga                                                    12436
```

<210> SEQ ID NO 2
<211> LENGTH: 429
<212> TYPE: PRT
<213> ORGANISM: Homo sapiens

<400> SEQUENCE: 2

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Ala Arg Thr Pro Thr Met Gly Trp Leu His Trp Glu
            35                  40                  45

Arg Phe Met Cys Asn Leu Asp Cys Gln Glu Glu Pro Asp Ser Cys Ile
        50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140
```

-continued

```
Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
            275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
                340                 345                 350

Met Ile Asn Arg Gln Glu Ile Gly Gly Pro Arg Ser Tyr Thr Ile Ala
            355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425
```